US007807662B2

(12) United States Patent
Turkson et al.

(10) Patent No.: US 7,807,662 B2
(45) Date of Patent: Oct. 5, 2010

(54) PLATINUM IV COMPLEX INHIBITOR

(75) Inventors: James Turkson, Orlando, FL (US); Richard Jove, Glendora, CA (US); Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 46 days.

(21) Appl. No.: 11/317,516

(22) Filed: Dec. 23, 2005

(65) Prior Publication Data
US 2007/0123502 A1 May 31, 2007

Related U.S. Application Data

(60) Provisional application No. 60/593,229, filed on Dec. 23, 2004.

(51) Int. Cl.
*A61K 31/33* (2006.01)
*A61K 31/545* (2006.01)
*A01N 55/102* (2006.01)

(52) U.S. Cl. .................. 514/183; 514/184; 514/202
(58) Field of Classification Search .............. 514/183, 514/184, 202
See application file for complete search history.

(56) References Cited

U.S. PATENT DOCUMENTS

2004/0097423 A1  5/2004 Siddik et al.
2006/0030536 A1* 2/2006 Yu et al. ................ 514/44

FOREIGN PATENT DOCUMENTS

WO  WO-2006/071812 A2  7/2006

OTHER PUBLICATIONS

Akira, S. (2000). "Roles of STAT3 Defined by Tissue-Specific Gene Targeting," *Oncogene* 19:2607-2611.
Allain, P. et al. (2000). "Early Biotransformations of Oxaliplatin After its Intravenous Administration to Cancer Patients," *Drug Metab Dispos* 28(11):1379-1384.
Becker, S. et al. (1998). "Three-Dimensional Structure of the Stat3β Homodimer Bound to DNA," *Nature* 394:145-151.
Bose, R.N. (2002). "Biomolecular Targets for Platinum Antitumor Drugs," *Mini. Rev. Med. Chem.* 2(2):103-111.
Bowman, T. et al. (Jun. 19, 2001). "Stat3-Mediated Myc Expression is Required for Src Transformation and PDGF-Induced Mitogenesis," *Proc. Natl. Acad. Sci. U. S. A.* 98(13):7319-7324.
Bowman, T. et al. (2000). "STATs in Oncogenesis," *Oncogene* 19:2474-2488.
Bromberg, J. (2000). "Signal Transducers and Activators of Transcription as Regulators of Growth, Apoptosis and Breast Development," *Breast Cancer Res.* 2:86-90.
Bromberg, J. F. et al. (May 1998). "Stat3 Activation is Required for Cellular Transformation by v-*src*," *Mol. Cell. Biol.* 18(5):2553-2558.
Bromberg, J. F. et al. (Jul. 1996). "Transcriptionally Active Stat1 is Required for the Antiproliferative Effects of Both Interferon α and Interferon γ," *Proc. Natl. Acad. Sci. USA* 93:7673-7678.
Bromberg, J. F. et al. (Aug. 6, 1999). "Stat3 as an Oncogene," *Cell* 98:295-303.
Buettner, R. et al. (Apr. 2002). "Activated STAT Signaling in Human Tumors Provides Novel Molecular Targets for Therapeutic Intervention," *Clin. Cancer Res.* 8:945-954.
Catlett-Falcone, R. et al. (Jan. 1999). "Constitutive Activation of Stat3 Signaling Confers Resistance to Apoptosis in Human U266 Myeloma Cells," *Immunity* 10:105-115.
Coffer, P. J. et al. (2000). "The Role of STATs in Myeloid Differentiation and Leukemia," *Oncogene* 19:2511-2522.
Darnell, J. E., Jr. (Sep. 12, 1997). "STATs and Gene Regulation," *Science* 277:1630-1635.
Darnell, J. E., Jr. (Oct. 2002). "Transcription Factors as Targets for Cancer Therapy," *Nat. Rev. Cancer* 2:740-749.
Darnell, J. E., Jr. et al. (Jun. 3, 1994). "Jak-STAT Pathways and Transcriptional Activation in Response to IFNs and Other Extracellular Signaling Proteins," *Science* 264:1415-1421.
Epling-Burnette, P. K. et al. (Feb. 2001). "Inhibition of STAT3 Signaling Leads to Apoptosis of Leukemic Large Granular Lymphocytes and Decreased Mcl-1 Expression," *J. Clin. Invest.* 107(3):351-362.
Fukada, T. et al. (Nov. 1996). "Two Signals are Necessary for Cell Proliferation Induced by a Cytokine Receptor gp130: Involvement of STAT3 in Anti-Apoptosis," *Immunity* 5:449-460.
Garcia, R. et al. (2001). "Constitutive Activation of Stat3 by the Src and JAK Tyrosine Kinases Participates in Growth Regulation of Human Breast Carcinoma Cells," *Oncogene* 20:2499-2513.
Garcia, R. et al. (Dec. 1997). "Constitutive Activation of Stat3 in Fibroblasts Transformed by Diverse Oncoproteins and in Breast Carcinoma Cells," *Cell Growth Diff.* 8:1267-1276.
Gouilleux, F. et al. (1995). "Prolactin and Interleukin-2 Receptors in T Lymphocytes Signal through a MFG-STAT5-Like Transcription Factor," *Endocrinology* 136(12):5700-5708.
Grandis, J. R. et al. (Apr. 11, 2000). "Constitutive Activation of Stat3 Signaling Abrogates Apoptosis in Squamous Cell Carcinogenesis in Vivo," *Proc. Natl. Acad. Sci. U.S.A.* 97(8):4227-4232.
Heudi, O. et al. (2001). "Chemical Instability and Methods for Measurement of Cisplatin Adducts Formed by Interactions with Cysteine and Glutathione," *Int J Clin Pharmacol Ther* 39(8):344-349.
Heudi, O. et al. (1999). "Mechanisms of Reaction of L-Methionine with Carboplatin and Oxaliplatin in Different Media: a Comparison with Cisplatin," *Biopharm Drug Dispos* 20:107-116.
Hirano, T. et al. (2000). "Roles of STAT3 in Mediating the Cell Growth, Differentiation and Survival Signals Relayed Through the IL-6 Family of Cytokine Receptors," *Oncogene* 19:2548-2556.
Johnson, P. J. et al. (May 1985). "Overexpressed pp60$^{c-src}$ Can Induce Focus Formation Without Complete Transformation of NIH 3T3 Cells," *Mol. Cell. Biol.* 5(5):1073-1083.
Kotenko, S. V. et al. (2000). "Jak-Stat Signal Transduction Pathway Through the Eyes of Cytokine Class II Receptor Complexes," *Oncogene* 19:2557-2565.
Lin, T. S. et al. (2000). "STAT Signaling in the Pathogenesis and Treatment of Leukemias," *Oncogene* 19:2496-2504.

(Continued)

*Primary Examiner*—Brandon J Fetterolf
*Assistant Examiner*—Anna Pagonakis
(74) *Attorney, Agent, or Firm*—Morrison & Foerster LLP

(57) ABSTRACT

The invention disclosed herein provides methods for diagnosing and treating diseases and/or conditions associated with dysregulated Stat3-mediated activity.

7 Claims, 6 Drawing Sheets

OTHER PUBLICATIONS

Mora, L. B. et al. (Nov. 15, 2002). "Constitutive Activation of Stat3 in Human Prostate Tumors and Cell Lines: Direct Inhibition of Stat3 Signaling Induces Apoptosis of Prostate Cancer Cells," *Cancer Res* 62:6659-6666.

Nielsen, M. et al. (1999). "Inhibition of Constitutively Activated Stat3 Correlates with Altered Bcl-2/Bax Expression and Induction of Apoptosis in Mycosis Fungoides Tumor Cells," *Leukemia* 13:735-738.

Nielsen, M. et al. (Jun. 1997). "Constitutive Activation of a Slowly Migrating Isoform of Stat3 in Mycosis Fungoides: Tyrphostin AG490 Inhibits Stat3 Activation and Growth of Mycosis Fungoides Tumor Cell Lines," *Proc. Natl. Acad. Sci. USA* 94:6764-6769.

Niu, G. et al. (Oct. 15, 1999). "Gene Therapy with Dominant-Negative Stat3 Suppresses Growth of the Murine Melanoma B16 Tumor in vivo," *Cancer Res.* 59:5059-5063.

Oshiro, M. M. et al. (Dec. 2001). "Inhibition of JAK Kinase Activity Enhances Fas-Mediated Apoptosis but Reduces Cytotoxic Activity of Topoisomerase II Inhibitors in U266 Myeloma Cells," *Clin. Cancer Res.* 7:4262-4271.

Oyajobi, B. O. et al. (Jul. 1, 2003). "Dual Effects of Macrophage Inflammatory Protein-1α on Osteolysis and Tumor Burden in the Murine 5TGM1 Model of Myeloma Bone Disease," *Blood* 102(1): 311-319.

Perez, J. M. et al. (2003). "Antitumor and Cellular Pharmacological Properties of a Novel Platinum(IV) Complex: *trans*-[PtCl$_2$(OH)$_2$ (Dimethylamine) (Isopropylamine)]," *Mol Pharmacol* 63(4):933-944.

Persons, D. L. et al. (May 1999). "Cisplatin-Induced Activation of Mitogen-Activated Protein Kinases in Ovarian Carcinoma Cells: Inhibition of Extracellular Signal-Regulated Kinase Activity Increases Sensitivity to Cisplatin," *Clin. Cancer. Res.* 5:1007-1014.

Sanchez-Perez, I. et al. (1998). "Cisplatin Induces a Persistant Activation of JNK that is Related to Cell Death," *Oncogene* 16:533-540.

Schindler, C. et al. (1995). "Transcriptional Responses to Polypeptide Ligands: the JAK-Stat Pathway," *Annu. Rev. Biochem.* 64:621-651.

Seidel, H. M. et al. (Mar. 1995). "Spacing of Palindromic Half Sites as a Determinant of Selective STAT (Signal Transducers and Activators of Transcription) DNA Binding and Transcriptional Activity," *Proc. Natl. Acad. Sci. U. S. A.* 92:3041-3045.

Siddik, Z. H. (2003). "Cisplatin: Mode of Cytotoxic Action and Molecular Basis of Resistance," *Oncogene* 22: 7265-7279.

Sinibaldi, D. et al. (2000). "Induction of p$^{21}$WAF1/CIP1 and Cyclin D1 Expression by the Src Oncoprotein in Mouse Fibroblasts: Role of Activated STAT3 Signaling," *Oncogene* 19:5419-5427.

Smithgall, T. E. et al. (2000). "Control of Myeloid Differentiation and Survival by Stats," *Oncogene* 19:2612-2618.

Song, J. I. et al. (2000). "STAT Signaling in Head and Neck Cancer," *Oncogene* 19:2489-2495.

Song, L. et al. (2003). "Activation of Stat3 by Receptor Tyrosine Kinases and Cytokines Regulates Survival in Human Non-Small Cell Carcinoma Cells," *Oncogene* 22:4150-4165.

Stark, G. R. et al. (1998). "How Cells Respond to Interferons," *Annu. Rev. Biochem.* 67:227-264.

Trynda-Lemiesz, L. et al. (2004). "Human Serum Albumin: Spectroscopic Studies of the Paclitaxel Binding and Proximity Relationships with Cisplatin and Adriamycin," *J Inorg Biochem* 98:1851-1856.

Trynda-Lemiesz, L. et al. (1999). "Effect of *cis*-, *trans*-Diamminedichloroplatinum(II) and DBP on Human Serum Albumin," *J Inorg Biochem* 77:141-146.

Turkson, J. (2004). "STAT Proteins as Novel Targets for Cancer Drug Discovery," *Expert Opin Ther Targets* 8:409-422.

Turkson, J. et al. (2000). "STAT Proteins: Novel Molecular Targets for Cancer Drug Discovery," *Oncogene* 19:6613-6626.

Turkson, J. et al. (May 1998). "Stat3 Activation by Src Induces Specific Gene Regulation and is Required for Cell Transformation," *Mol. Cell. Biol.* 18(5):2545-2552.

Turkson, J. et al. (Nov. 1999). "Requirement for Ras/Rac1-Mediated p38 and c-Jun N-Terminal Kinase Signaling in Stat3 Transcriptional Activity Induced by SRC Oncoprotein," *Mol. Cell. Biol.* 19(11):7519-7528.

Turkson, J. et al. (Nov. 30, 2001). "Phosphotyrosyl Peptides Block Stat3-Mediated DNA Binding Activity, Gene Regulation, and Cell Transformation," *J. Biol. Chem.* 276(48):45443-45455.

Turkson, J. et al. (Dec. 2004). "Inhibition of Consitutive Signal Transducer and Activator of Transcription 3 Activation by Novel Platinum Complexes with Potent Antitumor Activity," *Mol. Cancer Ther.* 3(12):1533-1542.

Wagner, B. J. et al. (1990). "The SIF Binding Element Confers *sis*/PDGF Inducibility onto the c-*fos* Promoter," *EMBO J.* 9(13):4477-4484.

Wang, G. et al. (2004). "Molecular Basis of Cellular Response to Cisplatin Chemotherapy in Non-Small Cell Lung Cancer," *Oncol. Rep.* 12:955-965.

Yamauchi, K. et al. (Jul. 15, 1993). "Phosphadidylinositol 3-Kinase Functions Upstream of Ras and Raf in Mediating Insulin Stimulation of c-*fos* Transcription," *J. Biol. Chem.* 268(20):14597-14600.

Yu, C.-L. et al. (Jul. 7, 1995). "Enhanced DNA -Binding Activity of a Stat3-Related Protein in Cells Transformed by the Src Oncoprotein," *Science* 269:81-83.

Yu, H. et al. (Feb. 2004). "The Stats of Cancer—New Molecular Targets Come of Age," *Nat. Rev. Cancer* 4:97-105.

Zhang, D. et al. (Apr. 19, 1996). "STAT3 Participates in Transcriptional Activation of the C-Reactive Protein Gene by Interleukin-6," *J. Biol. Chem.* 271(16):9503-9509.

Zhang, Y. et al. (Aug. 11, 2000). "Activation of Stat3 in v-Src-Transformed Fibroblasts Requires Cooperation of Jak1 Kinase Activity," *J. Biol. Chem.* 275(32):24935-24944.

Ferrante, K. et al. (1999). "Promising New Developments in Cancer Chemotherapy," *Cancer Chemother. Pharmacol.* 43(Suppl.):S61-S68.

Mellor, H.R. et al. (2005). "The Influence of Tumour Microenvironmental Factors on the Efficacy of Cisplatin and Novel Platinum(IV) Complexes," *Biochemical Pharmacology* 70:1137-1146.

Turkson, J. et al. (Sep. 2005). "A Novel Platinum Compound Inhibits Constitutive Stat3 Signaling and Induces Cell Cycle Arrest and Apoptosis of Malignant Cells," *Journal of Biological Chemistry* 280(38):32979-32988.

\* cited by examiner

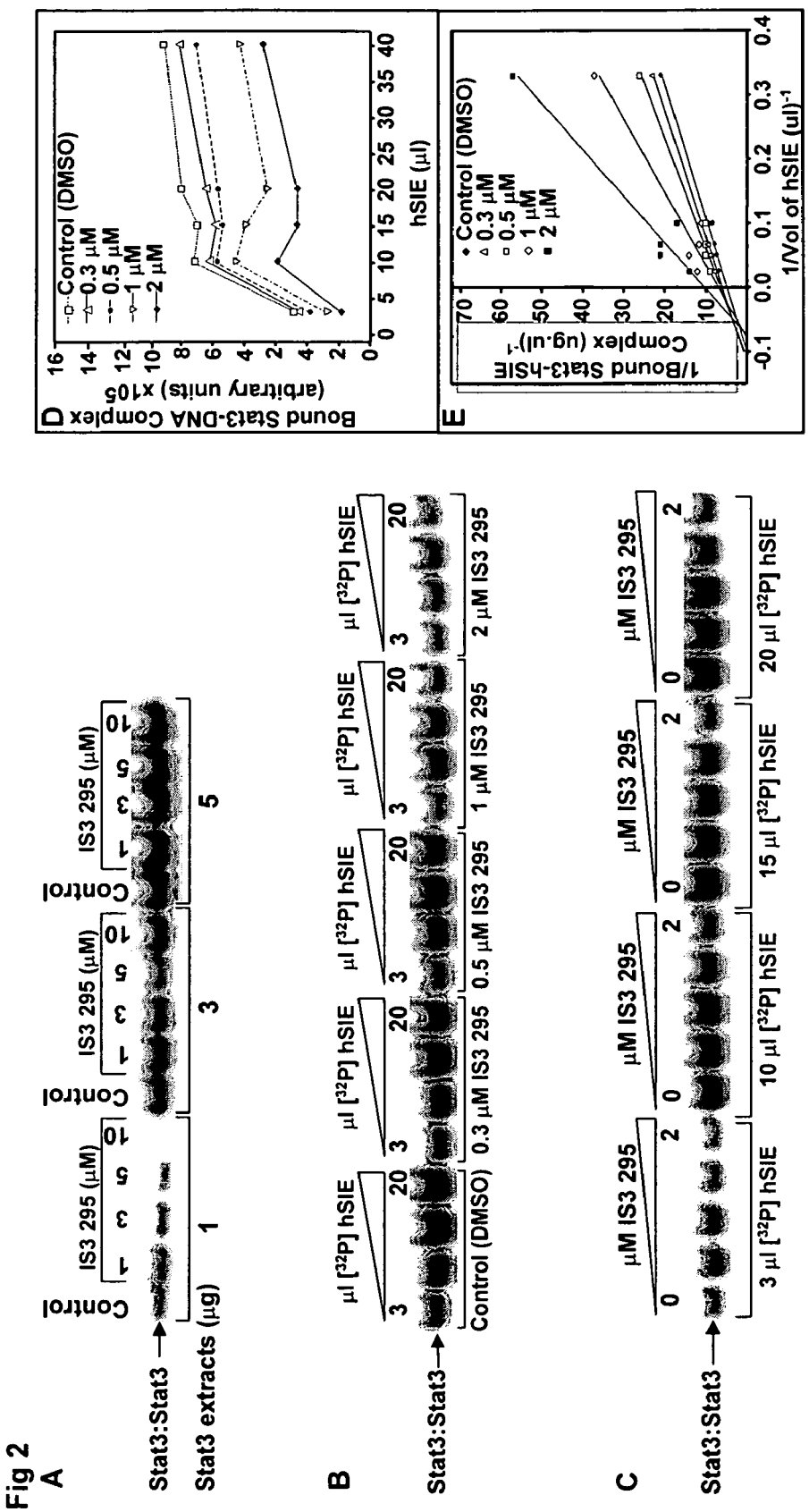

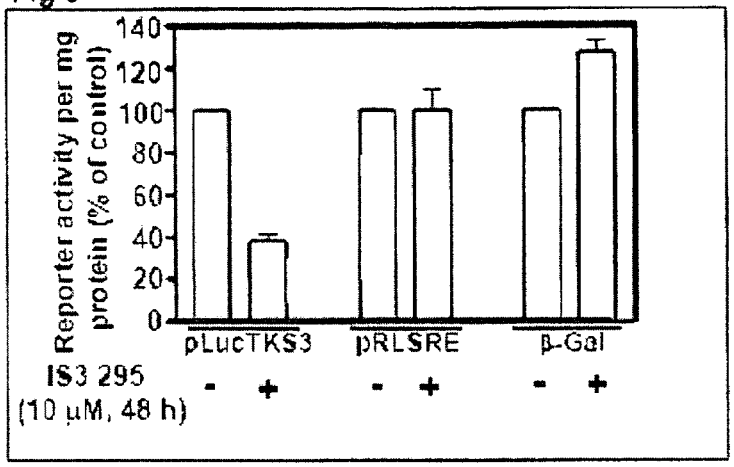
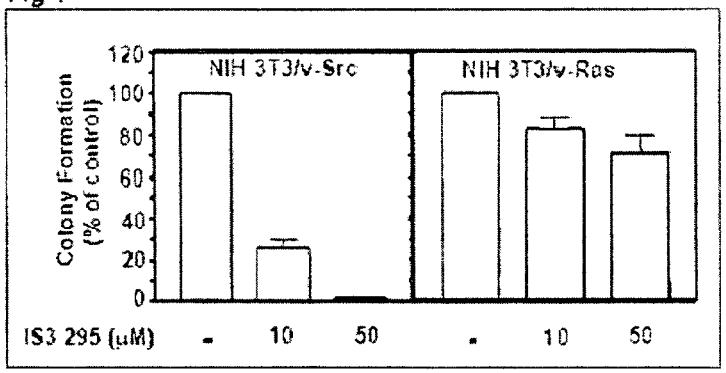
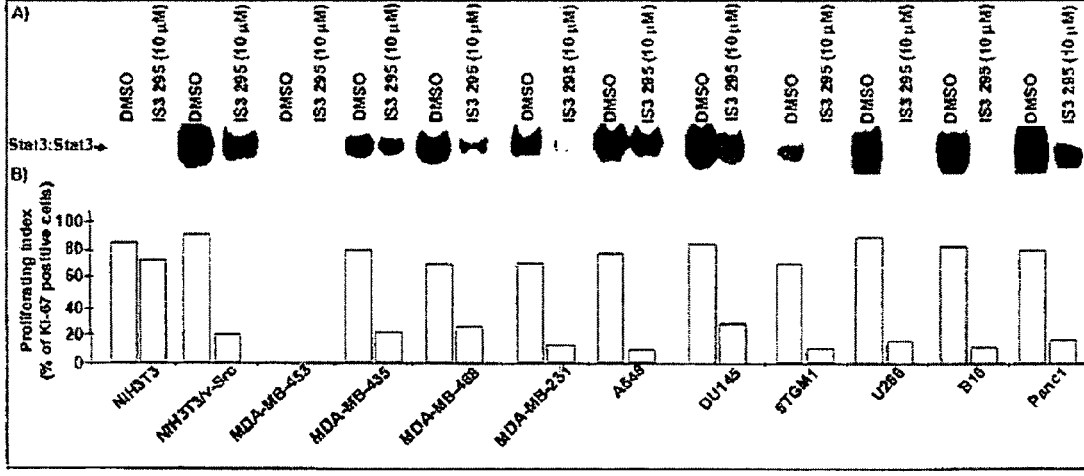

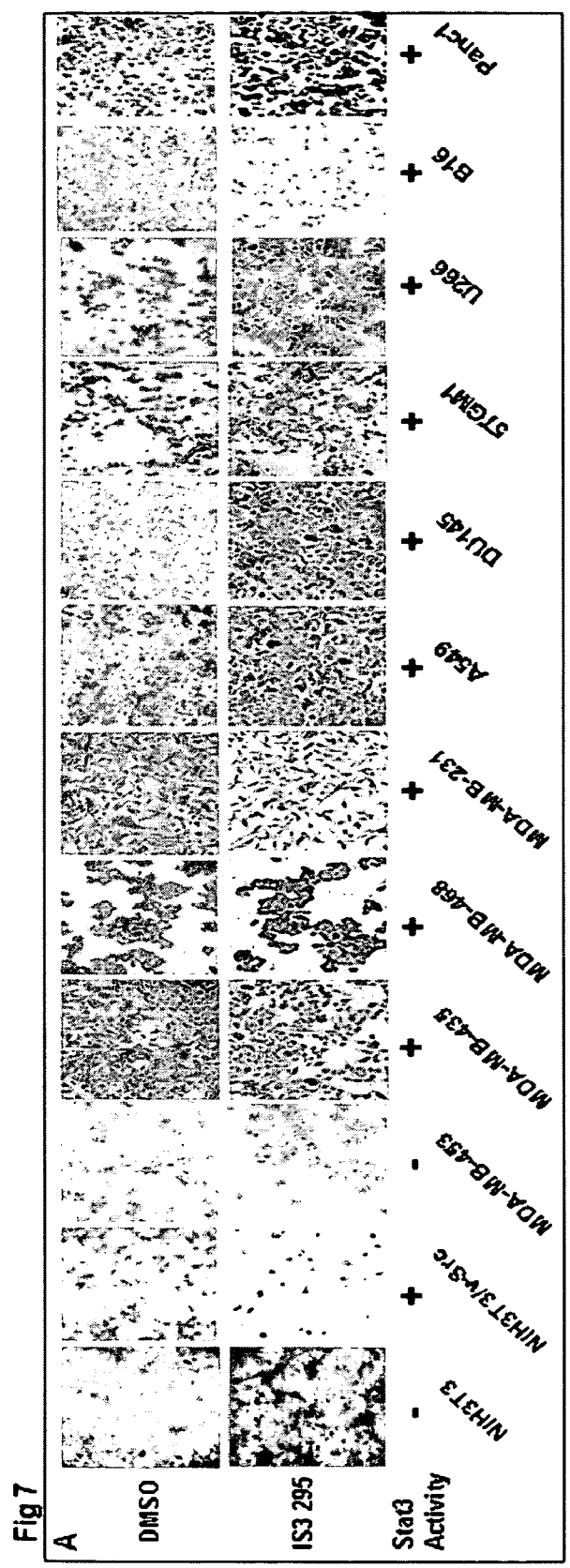

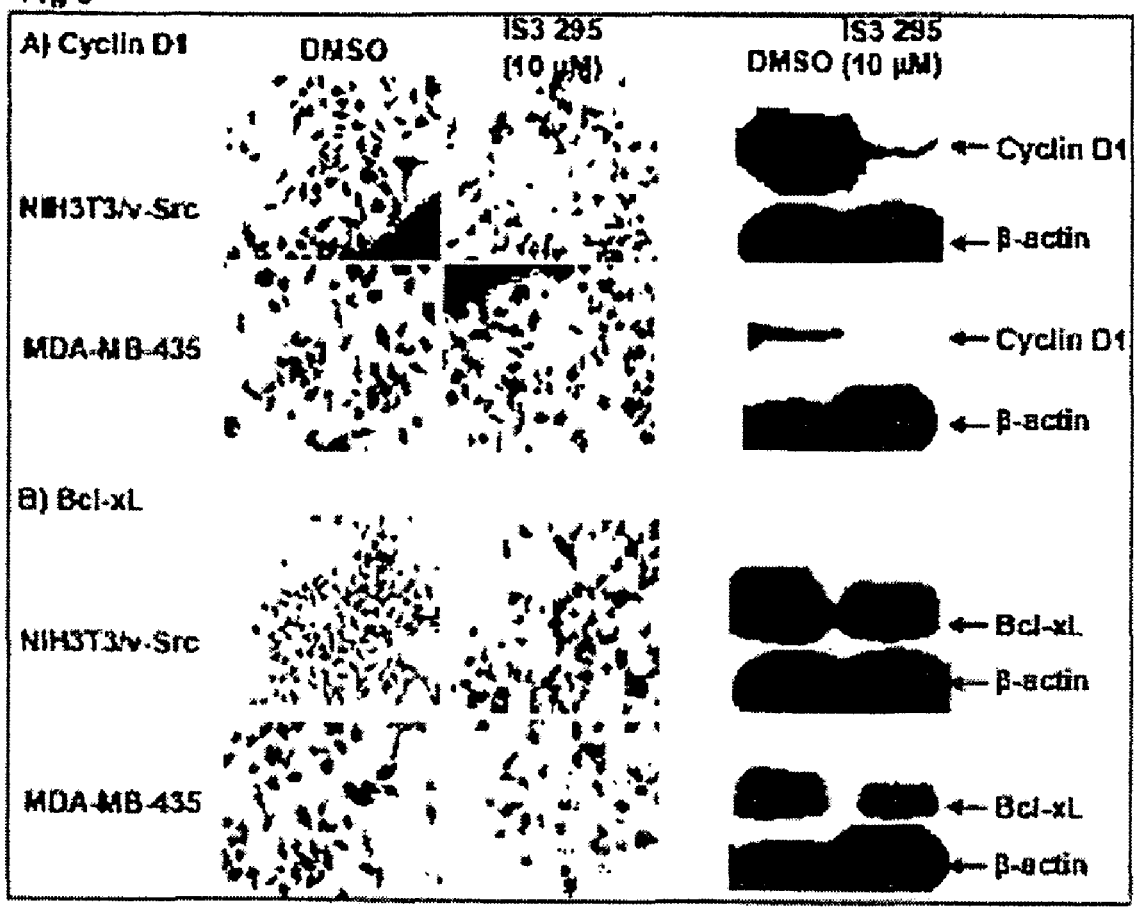

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
agcttcattt cccgtaaatc ccta                                              24

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
agatttctag gaattcaa                                                     18

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gctccagcat ctgctgcttc                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
gctccaatac ccgttgcttc                                                   20
```

PLATINUM IV COMPLEX INHIBITOR

RELATED APPLICATIONS

This application claims priority to U.S. provisional application 60/593,229, filed on Dec. 23, 2004. The provisional application is incorporated herein in its entirety by reference.

STATEMENT OF GOVERNMENT INTEREST

This invention was made with government support under 5P01-CA78038 awarded by the National Cancer Institute. The government has certain rights in the invention.

TECHNICAL FIELD

The invention relates to the use of a platinum (IV) compound, IS3 295, to treat undesired or dysregulated Stat3-mediated cell growth. More specifically, the invention provides for the inhibition of Stat3 and its biological activity by a platinum (IV) complex. The invention identifies a new application for a class of platinum (IV) complexes as a direct modulator of Stat3 pathway that abrogates the abnormal gene expression and the consequent dysregulated growth and survival owing to aberrant Stat3 activity.

BACKGROUND OF THE INVENTION

Cellular responses to growth factors and cytokines are characterized by the activation of signal transduction pathways, including the signal transducer and activator of transcription (Stat) family of cytoplasmic transcription factors (1-4). Activation of Stat proteins is initiated upon their tyrosine phosphorylation, a key event in the formation of phosphotyrosine-SH2 (pTyr-SH2) interactions and the dimerization between two Stat monomers. In turn, dimers of Stats translocate to the nucleus and bind to specific DNA-response elements and induce the transcription of genes essential for cellular responses. Physiological functions of Stats include cell proliferation, differentiation, development and apoptosis (reviewed in (5-10)).

In contrast to the finite kinetics of normal Stat signaling, constitutive activation of Stat3 and Stat5 is frequently observed in human tumors (11, 12) and has been linked to tumor progression. Aberrant Stat3 signaling is detected in breast cancer, prostate cancer, head and neck squamous cell carcinoma, as well as in lymphomas and leukemias (13-20, reviewed in 21-28). In malignant cell lines and tumors that harbor constitutively active Stat3, studies also show an overexpression of Stat3-regulated genes, including anti-apoptotic Bcl-xL, Mcl-1, Bcl-2, and survivin, cell cycle regulators, Cyclin D1 and D2, angiogenesis factor, VEGF, and altered expression of immune-modulatory factors (15, 16, 18, 20). These abnormal changes lead to the dysregulated biological processes, cell cycle, survival and angiogenesis, and the repressed host immune functions (reviewed in (27, 28) that contribute to oncogenic transformation. Thus, the inhibition of abnormal Stat3 signaling alone is sufficient to repress the induction of these genes, resulting in cell cycle arrests and apoptosis of malignant cells (15, 18, 20, 29), sensitization of tumor cells to chemotherapy-induced apoptosis (30), and tumor regression (29). Small-molecule inhibitors of Stat3 therefore have the potential to impact tumors that harbor constitutively active Stat3.

Some studies have established constitutive activation of Stat3 as one of the molecular changes that is required for tumor development and progression. Other studies have implicated signal transduction components in the antitumor cell activity of platinum complexes. There is evidence to suggest the modulation by cisplatin of members of the mitogen-activated protein kinase family and PI-3-kinase/Akt (31-34). Importantly, cisplatin does not have an effect on Stat3 activity. Although a compound may contain platinum, the effect of each platinum-containing compound on malignant cells differs, thus making it difficult to predict how effective a certain platinum-containing compound will be on a particular type of cancer a priori. Nonetheless, the wide therapeutic application of cisplatin in solid tumors (34, 51) and the importance of constitutively active Stat3 in malignant transformation together make the present invention of great significance in its exploration of the biochemical and biological properties of IS3 295 as a Stat3 inhibitor.

A previous study reported that a different class of platinum complexes inhibited Stat3 signaling and induced tumor regression (35). The current invention improves upon the report (35) and investigated the modulation of Stat3 by a different platinum compound and how this contributes to the anti-tumor cell activity in vivo.

BRIEF SUMMARY OF THE INVENTION

The invention provides for a method of inducing apoptosis in a malignant cell comprising contacting the malignant cell with IS3 295. In one embodiment, the malignant cell is selected from the group consisting of breast cancer, prostate cancer, head and neck squamous cell carcinoma, lymphoma, leukemia, multiple myeloma, glioma, non-small cell lung cancer, melanoma, gastrointestinal stromal tumor, renal cell carcinoma, esophageal carcinoma, ovarian cancer, cervical cancer and gastric cancer. In another embodiment, the malignant cell is a human cell. In another embodiment, the malignant cell is a non-human cell.

In another aspect, the invention provides for a method of inhibiting malignant cell growth in individuals in need thereof comprising administering to the individual an amount of IS3 295 effective for reducing malignant cell growth in the individual. In one embodiment, the malignant cell growth is selected from the group consisting of breast cancer, prostate cancer, head and neck squamous cell carcinoma, lymphoma, leukemia, multiple myeloma, glioma, non-small cell lung cancer, melanoma, gastrointestinal stromal tumor, renal cell carcinoma, esophageal carcinoma, ovarian cancer, cervical cancer and gastric cancer.

In another aspect, the invention provides for a method for treating an individual with a disease or condition characterized by undesired or constitutively active Stat3 expression comprising administering to the individual an amount of IS3 295 sufficient to inhibit the constitutively active Stat3 activity. In one embodiment, the disease or condition is selected from the group consisting of breast cancer, prostate cancer, head and neck squamous cell carcinoma, lymphoma, leukemia, multiple myeloma, glioma, non-small cell lung cancer, melanoma, gastrointestinal stromal tumor, renal cell carcinoma, esophageal carcinoma, ovarian cancer, cervical cancer and gastric cancer. In another embodiment, the inhibition of constitutively active Stat3 activity is indicated by a decrease in tumor size, tumor regression, decline in the rate of metastasis; inhibition of metastasis, or an inhibitory effect on angiogenesis.

In another aspect, the invention provides for a method of treating an individual with a disease or condition characterized by the abnormal expression of at least one Stat3-regulated gene comprising administering to the individual an amount of IS3 295 sufficient to abrogate the abnormal expression of the Stat3-regulated gene in the individual. In one embodiment, the Stat-regulated gene is selected from the group consisting of Bcl-xL, Bcl-2, Mcl-1, cyclin D1, c-Myc, VEGF, immune modulatory factors, surviving, AKT-2, p53, and matrix metalloprotease-6. In another embodiment, the disease or condition is cancer. In yet another embodiment, the cancer is selected from the group consisting of breast cancer, prostate cancer, head and neck squamous cell carcinoma, lymphoma, leukemia, multiple myeloma, glioma, non-small cell lung cancer, melanoma, gastrointestinal stromal tumor, renal cell carcinoma, esophageal carcinoma, ovarian cancer, cervical cancer and gastric cancer. In another embodiment, the abrogation of the abnormal expression of the Stat3-regulated gene is indicated by a decrease in tumor size, tumor regression, decline in the rate of metastasis, inhibition of metastasis, or an inhibitory effect on angiogenesis.

In another aspect, the invention provides for a method for suppressing tumor growth comprising contacting a tumor cell with IS3 295 in an amount sufficient to suppress the tumor growth. In one embodiment, the tumor growth is selected from the group consisting of breast cancer, prostate cancer, head and neck squamous cell carcinoma, lymphoma, leukemia, multiple myeloma, glioma, non-small cell lung cancer, melanoma, gastrointestinal stromal tumor, renal cell carcinoma, esophageal carcinoma, ovarian cancer, cervical cancer and gastric cancer. In another embodiment, the contact between the tumor cell and IS3 295 is in vitro. In another embodiment, the contact between the tumor cell and IS3 295 is in vivo. In another embodiment, the suppression of tumor growth is indicated by a decrease in tumor size, tumor regression, decline in the rate of metastasis, inhibition of metastasis, or an inhibitory effect on angiogenesis.

In another aspect, the invention provides for a method of enhancing the sensitivity of a malignant cell to radiation comprising contacting a malignant cell with IS3 295 in an amount sufficient to make the malignant cell more susceptible to radiation than without exposure to IS3 295. In one embodiment, the malignant cell expresses constitutively active Stat3. In another embodiment, the radiation treatment is additionally used to abrogate the growth of malignant cells.

In another aspect, the invention provides for a method of enhancing the sensitivity of a malignant cell to chemotherapy comprising contacting a malignant cell with IS3 295 in an amount sufficient to make the malignant cell more susceptible to radiation than without exposure to IS3 295. In one embodiment, the malignant cell expresses constitutively active Stat3. In another embodiment, chemotherapy is additionally used to abrogate the growth of malignant cells.

In another aspect, the invention provides for a method of treating an individual who is suffering from undesired Stat-3 regulated cell growth comprising administering to the individual an effective amount of IS3 295 and at least one other platinum compound. In one embodiment, the other platinum compound is also a platinum IV compound. In a further embodiment, the other platinum IV compound is cisplatin.

BRIEF DESCRIPTION OF THE DRAWINGS

FIG. 2—FIG. 2 shows the results of experiments testing the kinetics of inhibition of in vitro Stat3 DNA-binding activity by a platinum (IV) compound. Cell lysates containing activated Stat3 were incubated with or without the indicated concentrations of platinum complex IS3 295 in the presence of radiolabeled hSIE probe for 30 minutes at room temperature prior to EMSA analysis. (A) Binding activity of different amounts of Stat3 protein to hSIE probe; (B) Stat3 binding activity to hSIE probe in the presence of increasing levels of hSIE probe; (C) Stat3 binding activity to hSIE probe in the presence of increasing amounts of hSIE probe; (D) A plot of hSIE-bound Stat3:Stat3 complex versus levels of hSIE oligonucleotide probe; (E) A Lineweaver-Burke (double reciprocal) plot of hSIE-bound Stat3:Stat3 complex versus levels of hSIE. Positions of Stat:Stat-DNA complexes in gel are labeled. Cell lysates were prepared from recombinant baculovirus-infected Sf-9 cells as described in "Experimental Procedures" part of the Examples section.

FIG. 3—FIG. 3 shows the results of experiments on the inhibition of Stat3-mediated gene expression in intact cells by platinum (IV) complex. v-Src-transformed mouse fibroblasts that stably express Stat3-dependent (NIH3T3/v-Src/pLucTKS 3) and Stat3-independent (NIH3T3/v-Src/pRLSRE) luciferase reporters or β-galactosidase expression vector were treated with or without IS3 295 for 48 hours. Cytosolic extracts were then prepared from cells for Stat3-dependent firefly luciferase activity, Stat3-independent renilla luciferase activity, and β-gal activity measurements. Values are the means and S.D. of three to five independent assays.

FIG. 4—FIG. 4 shows the results from experiments testing the effects of platinum (IV) compound on cell transformation. The suppression of growth of Stat3-dependent v-Src-transformed fibroblasts (NIH3T3/v-Src) in soft agar by IS3 295 (left panel) but not of Stat3-independent v-Ras transformed counterparts (NIH3T3/v-Ras) (right panel). Viral Src-transformed NIH3T3/v-Src or Ras-transformed NIH3T3/v-Ras fibroblasts were seeded in soft agar and treated every 2-3 days with or without the indicated concentrations of IS3 295 until large colonies were evident. Number of colonies of IS3 295-treated cells in soft agar were counted and expressed as % of control (non-treated) cells. Values are the mean and S.D. of the three independent assays.

FIG. 5—FIG. 5 shows the results of experiments on the effects of platinum (IV) complex on constitutive Stat3 activation and cell proliferation. Normal or malignant cells were treated with or without IS3 295 and nuclear extracts were prepared for DNA-binding activity and EMSA analysis, or cells were processed for Ki67 proliferation index assay quantified by immunohistochemistry. (A) EMSA analysis of Stat3 DNA-binding activity in nuclear extracts prepared from cells using radiolabeled hSIE; (B) Graphical representations of quantified nuclear staining for proliferation index (Ki-67) in cells. Stat3:Stat3-DNA complexes in gels are labeled. The presence of Ki-67 nuclear staining was calculated as the percent positive tumor cells in relation to the total number cells. Values for Ki-67 are representative of two independent assays.

FIG. 7—FIG. 7 shows the results involving experiments using TUNEL analysis for apoptosis induced by platinum (IV) complex. Normal NIH3T3 fibroblasts and their v-Src-transformed counterparts, human breast carcinoma cell lines (MDA-MB-453, MDA-MB-435, MDA-MB-468, and MDA-MB-231), human non-small cell lung cancer cell line (A549), human prostate cancer cell line (DU145), multiple myeloma 5TGM1 (mouse) and U266 (human) cell lines, mouse melanoma cell line (B16) and human pancreatic cancer cell line (Panc1) were treated with or without platinum complex for 48 hours and analyzed for evidence of DNA damage using TUNEL staining kit (upper panel). The incidence of activated Stat3 status is shown in lower panel. (−), no constitutively active Stat3; (+), constitutively active Stat3. Data are representative of three independent determinations.

FIG. 8—FIG. 8 shows the results for experiments for determining the inhibition of cyclin D1 and Bcl-xL induction by platinum (IV) complex. Viral-Src-transformed fibroblast (NIH3T3/v-Src) and human breast cancer cell line MDA-MB-435 that contain constitutively-activated Stat3 were treated with or without platinum complexes for 24-48 hours. Cells were processed for staining by immunohistochemistry, or cell lysates were prepared from cells and subjected to 5% PAGE and Western blot analysis, as indicated in "Experimental Procedures" of the Examples section. (A) Detection of cyclin D1; (B) Detection of Bcl-xL. Positions of cyclin D1 and Bcl-xL proteins are shown. β-actin levels are shown for normalizing for equal total protein. Data are representative of 3 independent determinations.

DETAILED DESCRIPTION OF THE INVENTION

Figure 1:
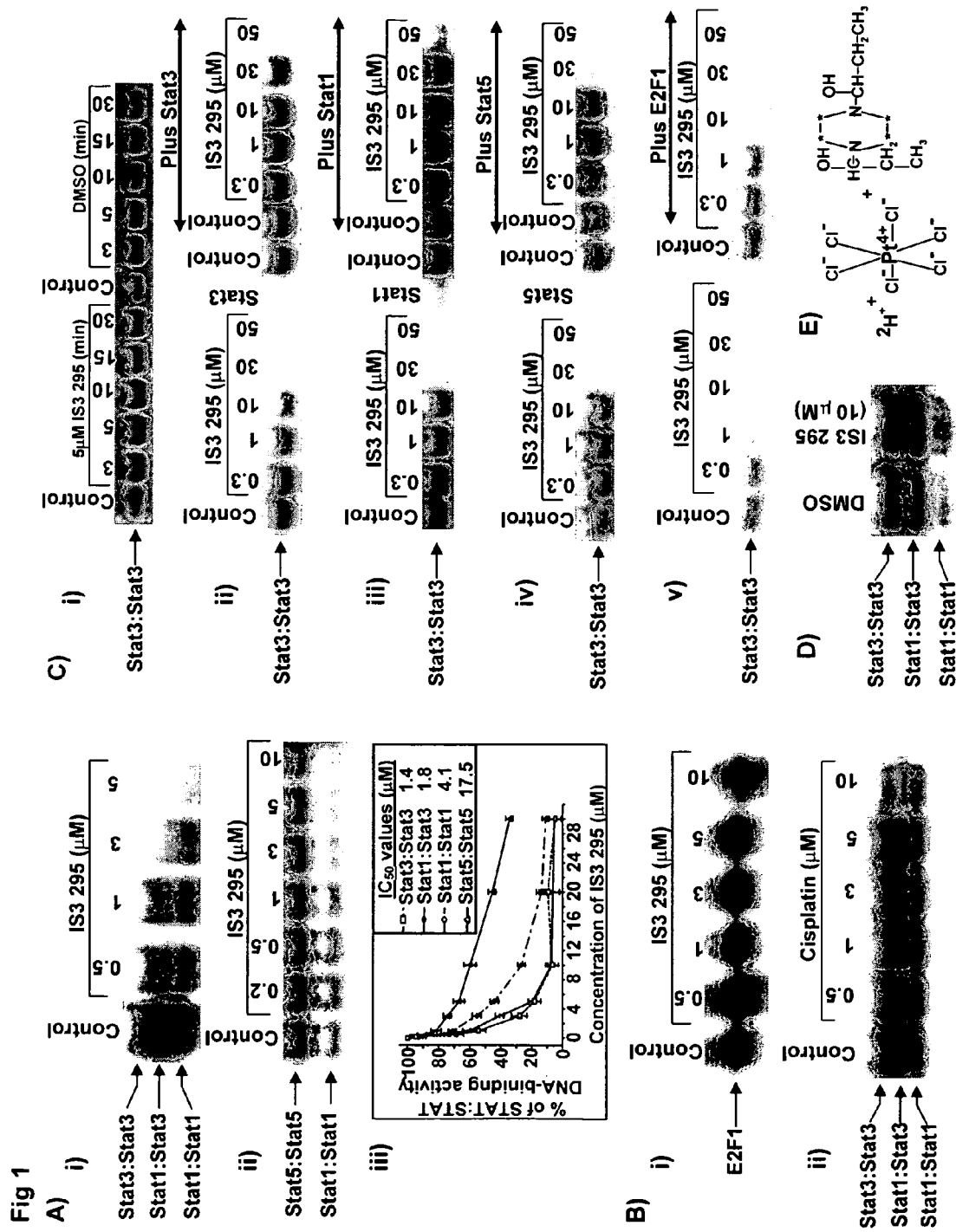
FIG. 1—FIG. 1 show the results of experiments on the inhibition of in vitro Stat3 DNA-binding activity by a platinum (IV) compound. Nuclear extracts containing activated Stat1, Stat3 and Stat5, or E2F1 were treated with or without the indicated concentrations of platinum complex IS3 295 or cisplatin for 30 minutes at room temperature prior to incubation with radiolabeled oligonucleotide probes. (A) (i) Stat1 and Stat3 binding activities to hSIE probe, (ii) Stat1 and Stat5 binding activities to MGFe probe, and (iii) plot of % DNA probe-bound Stat:Stat complex versus concentration of IS3 295. Insert shows $IC_{50}$ values for the inhibition of Stat:Stat DNA-binding activity; (B) (i) the binding of E2F1 to the dihydrofolate reductase promoter sequence as probe, and (ii) Stat1 and Stat3 binding activities to hSIE probe; (C) Stat3 binding activity to hSIE probe showing effects of (i) a prior incubation of probe with nuclear extract before the addition of IS3 295 or DMSO (vehicle), (ii) inactive Stat3 monomer, (iii) inactive Stat1 monomer, (iv) inactive Stat5 monomer, or (v) E2F1 protein; (D) Stat1 and Stat3 binding to IS3 295-treated and untreated radiolabeled hSIE probe; and (E) the structure of IS3 295. Positions of Stat:Stat-DNA complexes in gel are labeled. In (A) to (C), the control lanes represent nuclear extracts that are pre-incubated without platinum complex.

The invention provides for a novel use for a platinum (IV) complex, IS3 295, to treat diseases and conditions associated with constitutively active Stat3. The invention recognizes that IS3 295 can act as a modulator of Stat3 activity. This modulation can be used to effectuate various biological results. In addition, the ability to modulate Stat3 activity provides for therapeutic and other beneficial uses of IS3 295.

Platinum (IV) Complex, IS3 295

IS3 295 is a platinum (IV) complex which is characterized by the structure:

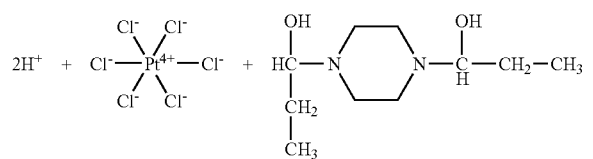

Compounds from an NCI diversity set were evaluated for being potential Stat3 inhibitors. This was accomplished by using in vitro DNA-binding activity assay with analysis of electrophoretic mobility shift assay (EMSA) to look for inhibition of Stat3 signaling. From these experiments (detailed in the Examples section), a platinum (IV) complex, IS3 295 (NSC 295558) was identified as potent inhibitor of Stat3.

Potential Interaction of IS3 295 with Stat3

The invention herein is based on a number of observations. One observation is that the administration of IS3 295 affects cells with constitutively active Stat3 activity but not inactive Stat3. Although IS3 295 binds to monomeric, inactive Stat3, no resulting biological effects are seen, such as tumor regression or apoptosis. In contrast, IS3 295 binding to activated, dimerized Stat3 results in some observerable biological changes. The activation of Stat3 to cause it form its dimeric form which then translocates to the nucleus includes not only constitutively active Stat3 forms (e.g., found in malignant, transformed cells) but also induced Stat3 forms (e.g., recombinant constructs).

Without being bound by theory, analyses of in vitro DNA-binding activity and transcriptional regulation show that IS3 295 interacts with Stat3, thereby inhibiting Stat3 binding to consensus DNA response element of the gene that is regulated by Stat3. Thus, an attenuating effect on Stat3-mediated transcriptional activity is seen when IS3 295 is administered. The attenuation can be a slight decrease in Stat3-mediated transcriptional activity, a medium decrease in Stat3-mediated transcriptional activity, a strong decrease in Stat3-mediated transcriptional activity, or it can be a complete abrogation of Stat3-mediated transcriptional activity.

Without being bound by theory, another possibility is that the interaction of IS3 295 with Stat3 changes the conformation of Stat3 in a manner that renders Stat3 unable to bind to the DNA response element and thus an attenuation of Stat3-mediated transcriptional activity is seen. As further detailed in the Examples section, binding analysis suggests non-competitive type kinetics of inhibition of binding to DNA.

Without being bound by theory, another possibility is that there is irreversible binding of IS3 295 to Stat3. In this embodiment of the invention, IS3 295 interacts with Stat3 in a way that changes Stat3 such that adding excess ligand (e.g., DNA) cannot rescue the inhibitory effect of IS3 295 on Stat3.

Studies have shown that cisplatin induces $G_2$-M block and apoptosis (34, 58), which are attributed to denaturation of DNA and formation of platinum-DNA adducts. Unlike the alkylating effects of cisplatin and related platinum complexes, there is minimal evidence of denaturation of the Stat3 consensus binding oligonucleotide sequence (hSIE). The Stat3-binding integrity of hSIE is preserved following treatment with IS3 295. Furthermore, oligonucleotide melting and re-annealing study indicated that the overall integrity of IS3 295-treated hSIE oligonucleotide is preserved. Thus, modulation of DNA is likely not a key factor in the inhibition of Stat3 signaling and biological functions by IS3 295.

The effects of IS3 295 also contrast that of cisplatin and others that modulate a variety of signal transduction components, including PI-3-kinase/Akt, MAPKs, JNK/p38mapk and JAKs, which contribute to their biological effects (31-34). The invention is based in part on the observation that IS3 295 has minimal effect on biological events that are independent of aberrant Stat3 signaling, including v-Ras transformation.

Biological Effects of IS3 295

The ability of IS3 295 to modulate the activity of Stat3 leads to downstream biological effects. In one embodiment, the invention is an attenuation of Stat3-mediated activity in the cells that have been contacted with IS3 295. In some cases, this attenuation affects transcriptional activity in the cell. In other instances, IS3 295 may affect downstream translational activity or post-translational activity in the cell. Generally, this modulation or attenuation results in observable biological effects, e.g., impact on the induction of Stat3-regulated genes. Examples of genes which may be affected by administration of IS3 295 include, but are not limited to, Bcl-xL, Bcl-2, Mcl-1, cyclin D1, c-Myc, VEGF, immune modulatory factors, survivin, AKT-2, p53, and matrix metalloprotease-6. Some of these genes are involved in the transformation of normal cells into malignant cells, which in turn results in some form of uncontrollable cancerous growth. Accordingly, in one embodiment, the invention provides for contacting a cell with IS3 295 to inhibit the malignant transformation of the cell. Some of these genes are involved in the ongoing malignancy of the cells, for example, VEGF is known to promote the angiogenesis of tumor cells. Accordingly, in another embodiment, the invention provides for contacting a malignant cell with IS3 295 to suppress the growth, expansion, or metastasis of malignant cells.

Constitutively active Stat3 mediates downstream genes critical for the dysregulated biological processes that contribute to malignant transformation. The induction of these genes are sensitive to Stat3 inhibition, as supported by current data of abrogation of the cell cycle control gene, cyclin D1 and the anti-apoptotic protein, Bcl-xL, and previous reports (15, 59, 60). Thus, modulation of aberrant Stat3 provides an approach to control critical aberrant molecular events that support the malignant phenotype. At the concentrations used, IS3 295 does not show general toxicity to normal or malignant cells that do not harbor constitutively active Stat3. The restriction of biological effects to cells harboring constitutively active Stat3 provides support for Stat3 protein as the primary target for IS3 295.

In another embodiment, the invention provides for methods for the inhibition of malignant cell growth seen in cells with constitutively active Stat3. This inhibition is achieved by contacting the malignant cells with IS3 295. This contact suppresses the induction of Stat3-regulated genes, including Bcl-xL and cyclin D1, two of the known Stat3-regulated genes that are overexpressed in malignant cells in part due to aberrant Stat3 activity and are key in subverting cell growth and apoptotic signals.

Another biological effect that is observed with administration of IS3 295 is a $G_0$-$G_1$ arrest in malignant cells treated with IS3 295. Yet another biological effect that is observed with administration of IS3 295 is apoptosis of malignant cells treated with IS3 295. Studies in v-Src-transformed fibroblasts as well as in human and mouse tumor cell lines that harbor constitutive Stat3 activity reveal a $G_0$-$G_1$ arrest and apoptosis following treatment with IS3 295, which correlate with the inhibition of aberrant Stat3 signaling.

The biological effects of IS3 295 are significantly evident in malignant cells harboring constitutively active Stat3 and not in cells lacking abnormal Stat3 activity. The Applicants have observed that only malignant cells (e.g., cells with dysregulated or undesired or uncontrolled growth) exhibit the $G_0$-$G_1$ arrest and/or apoptotic effect when exposed to IS3 295. Non-malignant cells, i.e., cells without dysregulated growth, do not exhibit the $G_0$-$G_1$ arrest and/or apoptotic effect when exposed to IS3 295. For example, due to the inhibition of constitutively active Stat3, IS3 295 abrogates the viral Src-transformation that is dependent on constitutive activation of Stat3, while not affecting events independent of aberrant Stat3 signaling. Also, the inhibition of cell growth and induction of apoptosis of malignant cells correlate with blockade of constitutive activation of Stat3. In breast cancer cell lines, IS3 295 induces cell cycle arrest and the pooling of cells at $G_0$-$G_1$ phase as well as a reduction in the S-phase. These observed effects parallel previous reports of the block of cell growth, as well as the repression of cell cycle and survival genes by blocking constitutively active Stat3 signaling (15, 19, 35, 49).

In human and mouse tumor cell lines and in transformed fibroblasts harboring constitutively active Stat3, IS3 295 selectively attenuates Stat3 signaling, consequently inhibiting malignant transformation, causing tumor cell growth arrest at $G_0$-$G_1$ phase, and inducing apoptosis. As detailed in the Examples, "selectively" means that IS3 295 has a greater effect on Stat3 than other Stat proteins, for example, the inhibitory effect of IS3 295 on Stat3 is three-fold higher than the inhibitory effect on Stat1. Thus, in one embodiment, the invention is a method for attenuating Stat3 signaling by contacting cells with constitutively active Stat3 with IS3 295 and then allowing for inhibition of malignant transformation.

In another embodiment, the cells with constitutively active Stat3 are contacted with IS3 295 to obtain tumor growth arrest. In yet another embodiment, the cells with constitutively active Stat3 are contacted with IS3 295 to get induction of apoptosis in these cells. These embodiments can be performed with cells in vitro, for example, with cells isolated from a patient or an individual in need of therapeutic treatment. In some cases, these cells can be re-introduced to the patient or individual in need of therapeutic treatment. Because IS3 295 does not affect cells with unactivated Stat3, exposure of normal cells to IS3 295 should not be affected significantly. Malignant cells exposed to IS3 295 are then eliminated and the remaining normal cell population can be re-introduced into the patient or individual in need of therapeutic treatment. Alternatively, the embodiments can be performed with cells in vivo, for example, administering IS3 295 to an individual. Cells which are contacted with IS3 295 may be human cells or in an alternative, non-human cells.

Diagnostic Uses of IS3 295

The ability of IS3 295 to modulate Stat3-mediated transcriptional activity also provides diagnostic uses for this platinum IV complex. In one aspect, the invention provides methods to diagnose malignant transformations or cancerous growth. Based on the Applicants' observation that only cells with activated Stat3 are negatively affected by IS3 295 but not cells with unactivated Stat3, one of ordinary skill in the art can diagnose the existence of malignant transformation by contacting the cells to IS3 295 and analyzing the results thereof. Procedures which may be used for analysis are further detailed in the Examples section and are known to one of ordinary skill in the art. One non-limiting example is to measure apoptotic effect by TUNEL assay. The observation that a sample of cells undergoes apoptosis upon exposure to IS3 295 could indicate that there was a Stat3-mediated transcription of some gene whose up-regulation has caused or will cause malignant transformation.

Other diagnostic uses of IS3 295 are also contemplated by the teachings within this disclosure and readily accomplished by those of ordinary skill in the art in following the teachings herein.

Therapeutic Uses of IS3 295

Signal transduction pathways and transcription factors have become increasingly significant to molecular-targeted approach to the development of cancer therapeutics because of their roles in cancer development (27, 28, 50). Previous reports have demonstrated the importance of constitutively active Stat3 in processes, such as dysregulated growth, survival, angiogenesis, and immune evasion, which contribute to tumorigenesis (22, 27).

Expression of Stat3 is constitutively active in some individuals who suffer from breast cancer, prostate cancer, head and neck squamous cell carcinoma, lymphoma, leukemia, multiple myeloma, glioma, non-small cell lung cancer, melanoma, gastrointestinal stromal tumor, renal cell carcinoma, esophageal carcinoma, ovarian cancer, cervical cancer or gastric cancer. The invention contemplates methods of treating these individuals by administration of IS3 295 in an amount sufficient to result in retardation or inhibition of malignant cell growth, tumor cell cycle arrest in the $G_0$-$G_1$ stage, and/or apoptosis of tumor cells. In one embodiment, a population of cells is isolated from the individual and exposed to IS3 295 and the biological effects of IS3 295 on malignant cells (discussed supra) are allowed to occur. The resulting cell population is then re-introduced into the individual.

Further, the invention provides for methods of treating an individual with a disease or condition characterized by undesired Stat3-mediated cell growth, such as that mediated by constitutively active Stat3 activity or induced active Stat3 activity. Examples of genes where active Stat3 activity could lead to malignant growth is discussed supra. For these genes, the downstream biological effect could be breast cancer, prostate cancer, head and neck squamous cell carcinoma, lymphoma, leukemia, multiple myeloma, glioma, non-small cell lung cancer, melanoma, gastrointestinal stromal tumor, renal cell carcinoma, esophageal carcinoma, ovarian cancer, cervical cancer and gastric cancer. Such treatment would involve administering IS3 295 sufficient to inhibit the growth of malignant cells whose aberrant growth is mediated in whole or in part by Stat3. In another embodiment, the invention is to induce apoptosis in malignant cells by administering an effective amount of IS3 295.

For the foregoing administration of IS3 295 alone, one of ordinary skill in the art can looks for the following indices to monitor the success of treatment plan and increase or decrease the amount administered accordingly. These indices include, but are not limited to, tumor size regression, change in of cell morphology from that of abnormal morphology to normal morphology, decline or inhibition of metastasis, decline or inhibition of angiogenesis. It will be apparent to one of skill in the art that these indices will vary depending on whether the cells which are exposed and/or contacted with IS3 295 are human cells or non-human cells.

Administration of IS3 295

Methods of administration can vary depending on what type of aberrant growth is being treated. For cutaneous conditions, a topical application would be appropriate. However, systemic administration of IS3 295 is also contemplated, for example by intravenous, oral, inhalant, parental, intraperitoneal, or topical methods of delivery.

The compound of the present invention may be administered as a composition, for example, as a pharmaceutical composition containing the compounds and a pharmaceutically-acceptable carrier or diluent. The IS3 295 can also be mixed with other active materials that do not impair the desired action and/or supplement the desired action. The active materials, in accordance with the present invention, may be administered by any acceptable route including, but not limited to, orally or parenterally (e.g., intravenously, intradermally, subcutaneously, intramuscularly, by an airborne delivery system, topically, etc.), in liquid or solid form.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. Suitable pharmaceutical carriers include, but are not limited to, sterile water; saline, dextrose; dextrose in water or saline.

Formulation and Dosages

The platinum IV complex disclosed herein can be formulated in various forms. In one embodiment, the IS3 295 is formulated according to the protocols commonly used by one of skill in the art. For example, since living cells are to be contacted with IS3 295, one of ordinary skill in the art would formulate IS3 295 in a manner that would not result in harm to the living cells. Accordingly, IS3 295 may be formulated using the some or all of the same ingredients that would normally be present in cell culture media for the particular cell type that is being used. In another embodiment, IS3 295 may be formulated in PBS at a dilution that does not harm or affect the biological activity of the cells to which IS3 295 contacts.

Formulation will vary for in vivo administration. One of skill in the art will appreciate the differences between the formulation needed for intravenous administration as contrasted with the formulation that would be optimal for another mode of administration, e.g., topical. As with in vitro protocols, one of ordinary skill in the art would take into consideration the need to formulate IS3 295 in a manner that does not cause toxicity in the individual, damage the individual to any appreciable degree or cause appreciable adverse side effects.

In another embodiment, IS3 295 is formulated according to methods known in the art for similar platinum IV complex, for example, cisplatin. It will be apparent to one of skill in the art how to modify the formulation without undue experimentation.

IS3 295 is administered to individuals in an amount sufficient to achieve the desired beneficial effects. In one embodiment, the desired effect is induction of apoptosis of malignant cells. In another embodiment, the desired effect is inducing a $G_0$-$G_1$ arrest of malignant cells. In other embodiments, the desired effects are to inhibit the transformation of cells, reduce and/or inhibit the growth of tumors, reduce and/or inhibit metastasis of cancerous cells. One of skill in the art would observe such indices or the indices disclosed supra and adjust the dosages accordingly.

The amount of IS3 295 administered in order to administer an sufficient amount to treat the disease or condition associated with dysregulated Stat3 activity will depend upon a variety of factors, including, for example, the particular condition being treated, the mode of administration, the severity of the condition being treated and the age and weight of the patient, the bioavailability of the composition, the adverse effects experienced by the individual being treated, etc. Determination of an effective dosage is well within the capabilities of those skilled in the art in view of the teachings provided herein. Dosages may also be estimated using in vivo animal models.

Kits Comprising IS3 295

The invention also provides for kits comprising IS3 295 in suitable formulations. The formulations may be in unit dosage amounts. Kits may further comprise suitable packaging and/or instructions for use of IS3 295 in diagnosing and treating diseases or condition associated with dysregulated Stat3-mediated activity. Kits may also comprise a means for the delivery of IS3 295, such as those known to a skilled artisan.

Combination Therapy

IS3 295 can be administered alone or in combination therapy with other treatments, for example, radiation therapy. In this embodiment, IS3 295 is administered first in time to sensitize cells to radiation therapy. The timing of IS3 295 administration with respect to radiation therapy is generally known by one skilled in the art of radiology and radiation treatment. In an alternative, IS3 295 is administered concurrently with radiation but IS3 295 is administered in an amount to make cells which were previously resistant to radiation therapy more sensitive to radiation treatment. In another alternative, IS3 295 can be administered after one or more initial round(s) of radiation proved to be ineffective. IS3 295 can be administered as many times as needed to achieve the desired beneficial results.

The invention provides methods for using IS3 295 as targeted chemotherapy in an individual in need of such therapy. In this case, the malignant cells which are exposed to IS3 295 become more susceptible to chemotherapy than they would have been had there not been any exposure to IS3 295. In one alternative, tumor cells are sensitized to chemotherapy by treatment with IS3 295 first. The timing of the administration of IS3 295 with respect to chemotherapy is generally known by one skilled in the art of chemotherapeutic treatment. The administration with IS3 295 can be simultaneous or progressive, depending on the type of cancer and responsiveness of the treatment. In another alternative, IS3 295 can be administered after one or more initial round(s) of chemotherapy proved to be ineffective. IS3 295 can be administered as many times as needed to achieve the desired beneficial results.

In another aspect, the invention contemplates combination therapy with another platinum-containing compound. One such compound that can be used is cisplatin. Administration of two or more platinum-containing compound would be in an amount sufficient to inhibit malignant cell growth or metastasis of the malignant cells. In another alternative, sufficient amount should be administered to induce the apoptosis or tumor cell cycle arrest in the $G_0$-$G_1$ stage.

For all of the foregoing combination therapies, one of skill in the art would evaluate the progress of such combination therapy by assessing, inter alia, tumor size regression, changes in cell morphology from that of abnormal morphology to normal morphology, decline or inhibition of metastasis, and/or decline or inhibition of angiogenesis. One of skill in the art will be able to recognize other indices that would indicate the positive effects that IS3 295 has on the individual to whom it has been administered.

The following examples are provided to further illustrate the invention; however, they should not be construed to limit the invention in any manner.

EXAMPLES

Example 1

Experimental Procedures

Cells and Reagents—Src-transformed NIH3T3/v-Src, NIH3T3/v-Src/pLucTKS3 and NIH3T3/v-Src/pRLSRE fibroblasts, human breast cancer (MDA-MB-231, MDA-MB-435, MDA-MB-453, and MDA-MB-468), human prostate cancer (DU145), multiple myeloma U266 (human) and 5TGM1 (mouse), mouse melanoma (B16), and human pancreatic cancer (Panc1) cell lines have all been previously described (15, 19, 29, 36-40). Cells were grown in Dulbecco's modified Eagle's medium (DMEM) containing 5% iron-supplemented bovine calf serum, with or without G418 or zeocin, or in RPMI containing 10% heat-inactivated fetal bovine serum.

Plasmids—The Stat3 reporter, pLucTKS3, driving the expression of firefly luciferase has been previously described (11, 41). The pLucTKS3 plasmid harbors seven copies of a sequence corresponding to the Stat3-specific binding site in the promoter of the human C-reactive protein gene (42). The plasmid, pRLSRE, contains two copies of the serum response element (SRE) from the c-fos promoter (11, 43), subcloned into the renilla luciferase reporter, pRL-null (Promega, Madison, Wis.).

Cytosolic extract preparation and luciferase assays—Cytosolic extract preparation from fibroblasts and luciferase assays were previously described (11, 41). Briefly, after two washes with PBS and equilibration for 5 minutes with 0.5 ml of PBS-0.5 mM EDTA, cells were scraped off the dishes and the cell pellet was obtained by centrifugation (4,500×g, 2 minutes, 4° C.). Cells were resuspended in 0.4 ml of low-salt HEPES buffer (10 mM HEPES (pH 7.8), 10 mM KCl, 0.1 mM EGTA, 0.1 mM EDTA, 1 mM phenylmethylsulfonyl fluoride (PMSF), and 1 mM dithiothreitol (DTT)) for 15 minutes, lysed by the addition of 20 µl of 10% Nonidet P-40 (NP-40), and centrifuged (10,000×g, 30 s, 4° C.) to obtain the cytosolic supernatant, which was used for luciferase assays (Promega) measured with a luminometer. Cytosolic lysates were prepared from baculovirus-infected Sf-9 cells for Stat3 protein, as previously described (44). Briefly, cultured dishes of Sf-9 cells were washed twice with ice-cold 1×PBS and then PBS containing 1 mM sodium orthovanadate. Cells were then lysed in 1% NP-40 lysis buffer (50 mM HEPES (pH 7.9), 150 mM NaCl, 1% NP-40, 20 mM NaF, 1 mM sodium orthovanadate, 1 mM tetrasodium pyrophosphate, 1 mM DTT, 0.5 mM PMSF, 2 mM EGTA, 2 mM EDTA, 0.1 µM aprotinin, 1 µM leupeptin, and 1 µM antipain) on ice for 10 minutes, and centrifuged (13,000×g, 30 s, 4° C.) to obtain lysate.

Nuclear extract preparation and gel shift assays—Nuclear extract preparation from v-Src-transformed fibroblasts (NIH3T3/v-Src) or tumor cell lines and electrophoretic mobility shift assay were carried out as previously described (11, 13, 37). The $^{32}$P-labeled oligonucleotide probes used were hSIE (high affinity sis-inducible element, m67 variant, 5'-AGCTTCATTTCCCGTAAATCCCTA) (SEQ ID NO:1) that bound Stat1 and Stat3 (13, 45) and MGFe (mammary gland factor element from the bovine β-casein gene promoter, 5'-AGATTTCTAGGAATTCAA) (SEQ ID NO:2) for Stat1 and Stat5 binding (46, 47). Except where indicated, inhibitor compound was pre-incubated with the nuclear extract for 30 minutes at room temperature prior to incubation with radiolabeled probe.

Western Blot—Whole-cell lysates were prepared in boiling sodium dodecyl sulfate (SDS) sample-loading buffer to extract total proteins from the cytoplasm and nucleus. Equivalent amounts of total cellular protein were electrophoresed on an SDS-10% polyacrylamide gel and transferred onto nitrocellulose membranes. Probing of nitrocellulose membranes with primary antibodies and detection of horseradish peroxidase-conjugated secondary antibodies by enhanced chemiluminescence (Amersham, Piscataway, N.J.) were performed as previously described (19, 35, 44). The probes used were anti-Cyclin D1 (Cell Signaling Technologies, Inc., Beverly, Mass.), anti-Bcl-xL (Cell Signaling Technologies, Inc.), and anti-β-Actin (Sigma-Aldrich, Co., St. Louis, Mo.).

Soft-agar colony formation assays—Colony formation assays were carried out in six-well dishes as previously described (41). In brief, each well contained 1.5 ml of 1% agarose in DMEM as the bottom layer, and 1.5 ml of 0.5% agarose in DMEM containing 4000 or 6000 NIH3T3/v-Src or NIH3T3/v-Ras fibroblasts, respectively, as the top layer. Treatment with IS3 295 was initiated 1 day after seeding cells by adding 75-100 µl of medium with or without compound, and repeated every three days, until large colonies were evident. Colonies were quantified by staining with 20 µl of 1 mg/ml iodonitrotetrazolium violet, incubating at 37° C. overnight and counting the next day.

Cell proliferation and TUNEL assays—Proliferating cells were first treated with or without IS3 295 for up to 48 hours. A portion of cells were harvested for BrdU incorporation following manufacturer's (BD Biosciences Pharmingen, San Diego, Calif.) instructions and analyzed by flow cytometry. Harvested cells were also analyzed for apoptosis via detection of TdT-mediated dUTP nick-end labeling (TUNEL) assay using Apoptosis Detection Systems Fluorescien according to the manufacturer's (Roche, Indianapolis, Ind.) instructions.

Oligonucleotides and plasmids Transfections—The Stat3 antisense (5'-<u>GCTCC</u>AGCATCTGCT <u>GCTTC</u>-3') (SEQ ID NO:3) or control mismatch oligonucleotides (5'-<u>GCTCC</u>AATACCCGTT <u>GCTTC</u>-3') (SEQ ID NO:4) were synthesized using phosphorothioate chemistry and were synthesized with 2'-O-methoxyethyl modification of the five terminal nucleotides (e.g., see underlined nucleotides above; (42, 51)) to increase stability. Transfections of Stat3 antisense (AS) and plasmids were carried out with Lipofectamine 2000 (LF) according to the manufacturer's instructions (Invitrogen, Carlsbad, Calif.). Briefly, cells were seeded at 1-2×10$^6$ cells/10-cm tissue-culture plates 18 hours before transfection. Immediately before transfection, cells were washed once with PBS. Cells were transfected with luciferase reporters (4 µg) in the presence or absence of v-Src (4 µg), or were transfected with Stat3β (4 µg) or pRC/CMV Stat3 Flag (4 µg). Stat3 AS transfections were carried out LF alone, or with LF/Stat3 antisense oligonucleotides, or LF/Stat3 mismatch oligonucleotides (final concentration of the oligonucleotides was 250 nM). After 2-3 hours, the transfection medium was aspirated and cells washed with PBS before fresh medium added containing 10% FBS was added. Forty-eight hours after transfection cells were washed and cytosolic lysates prepared for luciferase, as previously described (11, 41) or processed for TUNEL staining.

Immunohistochemistry—The indirect peroxidase-antiperoxidase test was performed on cytospin prepared from cell lines (control and treated). After inhibition of endogenous peroxidase with 0.3% $H_2O_2$ and methanol for 30 minutes, slides were rinsed in PBS (pH 7.4), treated for 30 minutes with 1.5% normal goat serum and then incubated for 1 hour with primary antibody against Ki-67 (Vector Laboratories, Inc., Burlingame, Calif.) at 1:100 dilution. Slides were then rinsed in PBS and incubated with biotinylated secondary antibody (Vector Laboratories, Inc) at 1:200 dilution for 30 minutes. Following washing with PBS, the preparations were further incubated in avidin-peroxidase conjugate (Vector Laboratories, Inc). The visualization was carried out with 3,3'-diaminobenzidine (Vector Laboratories, Inc) for 2 minutes. For microscopic evaluation, the preparations were counterstained with hematoxylin and mounted. Negative controls consisted of replacement of the primary antibody with PBS. The presence of Ki-67 nuclear staining was calculated as percent positive tumor cells in relation to the total number cells.

Example 2

Effect of IS3 295 on In Vitro DNA-Binding Activity of Stat3

Compounds from the NCI diversity set were evaluated for inhibition of Stat3 signaling in in vitro DNA-binding activity assay with analysis of electrophoretic mobility shift assay (EMSA). A platinum (IV) complex, IS3 295 (NSC 295558) (FIG. 1E), was identified as potent inhibitor of Stat3, which was further characterized in a number of assays for its anti-Stat3 property. In in vitro DNA-binding activity assay, nuclear extracts of equal total protein containing active Stat1, Stat3 and Stat5 were pre-incubated with different concentrations of IS3 295 for 30 minutes prior to incubation with $^{32}$P-labeled oligonucleotide, the m67 high affinity sis-inducible element (hSIE) probe that binds Stat1 and Stat3, or the mammary gland factor element (MGFe) that bound Stat1 and Stat5. Samples were then subjected to EMSA. Results showed that the presence of IS3 295 led to a dose-dependent reduction in the level of DNA-binding activity of Stat3:Stat3 (FIG. 1A (i), upper band), Stat1:Stat3 (FIG. 1A (i), intermediate band), and to a lesser extent of Stat1:Stat1 at three times higher concentration of IS3 295 (FIG. 1A (i) and (ii), lower band). In contrast, EMSA analysis showed that the presence of IS3 295 did not significantly affect the level of DNA-binding activity of Stat5:Stat5 dimers (FIG. 1A (ii), upper band). Together, these results indicated that IS3 295 was 3-fold more potent in disrupting Stat3 over Stat1 ($IC_{50}$ values of 1.4 µM and 4.1 µM, respectively, FIG. 1A (iii)), consistent with previous findings with other platinum (IV) complexes (35).

In control studies, the effect of IS3 295 was investigated on the DNA-binding activity of E2F1 that was unrelated to Stat proteins. Analysis by EMSA shows that pre-incubation with IS3 295 of cell lysates containing E2F1 prior to incubation with $^{32}$P-labeled dihydrofolate reductase (DHFR) promoter sequence as probe had no significant effect on the DNA-binding activity (FIG. 1B (i)). In another control study, effect of cisplatin was similarly evaluated on DNA-binding activities of Stat proteins and E2F1. cisplatin has no detectable effect on the levels of DNA-binding activities of Stat1 and Stat3 (FIG. 1B (ii)), on Stat5 (data not shown), or E2F1 DNA-binding activity in vitro. The findings together suggest that the effect on Stat3 is limited to IS3 295 and not a general phenomenon of all platinum compounds to inhibit the activities of transcription factors.

Example 3

Disruption of In Vitro Stat3 DNA-Binding Activity by IS3 295

The sequence of addition of reagents during the in vitro DNA-binding activity assay was changed to determine how the change would affect the kinetics of IS3 295-mediated inhibition of binding. Nuclear extracts containing activated Stat3 were first incubated with radiolabeled hSIE probe for 30 minutes to allow prior binding to oligonucleotide probe, followed by the addition of IS3 295 for additional 3-30 minutes, and subjected to EMSA analysis. IS3 295 failed to disrupt Stat3 DNA-binding activity when the protein was first bound to the DNA-response element probe (FIG. 1C (i), lanes 1-6 compare to control lanes 7-12). These findings indicated that pre-DNA-bound Stat3 protein was occluded from inhibition by IS3 295, suggesting that the Stat3 domain required for interaction with and inhibition by IS3 295 was inaccessible once the protein is already bound to DNA.

As such, without being restricted to this theory, one possibility is that IS3 295 bound Stat3 protein directly in a location on Stat3 protein that was required for Stat3 binding to the DNA response element of the gene that Stat3 regulated.

In other embodiment, without being bound to this theory, another possibility is that IS3 295 bound to Stat3 in a different location other than the exact sequences needed to bind to the DNA response element but in such a location that hindered the ability of the Stat3 protein to bind to the DNA response elements of the gene that Stat3 regulated.

In yet another embodiment, without being bound to this theory, another possibility is that IS3 295 bound to Stat3 and changed the conformation of Stat3 such that such a change in conformation hindered the ability of the Stat3 protein to bind to the DNA response elements of the gene that Stat3 regulated. In any event, the invention is not focused solely the mechanism of action but rather the resulting biological effect that IS3 295 has on Stat3-mediated cell regulation.

Differences in the modes of activity and selectivity are evident from that of cisplatin, which has no effect on Stat3 activity (35). Unlike with cisplatin, the experimented conducted indicate that IS3 295 interacted with Stat3 and inhibited its ability to bind to DNA response elements. While the exact site(s) within the Stat3 protein that interacts with IS3 295 is currently being investigated, preliminary data suggested it might be cysteine residues that react with IS3 295, however, it is to be understood that the inventors are not bound to this mechanism. Consistent with this, existing reports show cisplatin and other platinum complexes similarly interacted with serum albumin and γ-globulins (33, 52-54) via reaction with thiol-containing amino acids, cysteine and methionine, with which they form thiol conjugates of platinum complex (53, 55, 56). These reports (34, 53, 55, 56) raised the possibility that IS3 295 interacted with thiol-containing amino acids, possibly cysteine, within Stat3. Thus, in one embodiment, this modification in turn occludes the binding of the Stat3 protein to its consensus DNA response element.

The finding that prior binding of activated Stat3 to DNA consensus sequence eliminated the subsequent IS3 295-mediated inhibition, suggested that the pre-binding to DNA shielded the key amino acid residues within the protein from interacting with IS3 295. One possible theory is that both IS3 295 and DNA consensus sequence bound to the same domain of Stat3, which is the DNA-binding domain. Another possible theory is that protein conformational changes might have resulted from the prior binding to DNA response element probe, which restricted access to the key residues by IS3 295 for interaction. Indeed, the crystal structure of Stat3β bound to DNA (57) shows the Stat protein dimer clamped around the DNA double helix, akin to a pair of pliers, and this three dimensional structural arrangement possibly impeded any interaction of the protein with IS3 295. Additional support for interaction of IS3 295 with Stat3 also comes from the studies that the inactive Stat3 monomer protein but not non-Stat-related protein abolished the inhibitory effect of IS3 295, possibly by titrating out and diminishing the level of "free" IS3 295. Thus, this evidence supported the IS3 295 that interacts Stat3, which in turn blocks Stat3 DNA-binding activity, hence the biological functions of the protein.

Example 4

Interaction of IS3 295 with Monomeric Inactive Stat3 Protein

In another study, EMSA analysis showed that the simultaneous addition of IS3 295 and the hSIE probe to nuclear extracts containing activated Stat3 protein resulted in inhibition of Stat3 DNA-binding activity, as observed in FIG. 1A, suggesting a higher preference of Stat3 for IS3 295 over hSIE.

With the evidence suggesting a possible interaction of IS3 295 with Stat3 protein, the issue was whether inactive Stat monomer proteins, when supplied into the nuclear extract, could interact with IS3 295 and diminish its levels, thereby leaving free activated Stat3 protein for binding to hSIE probe. To address this issue, cell lysates of inactive Stat monomer proteins were added to nuclear extracts containing activated Stat3 and the mixture was preincubated with IS3 295 prior for 30 minutes prior to incubation with radiolabeled hSIE probe and EMSA analysis, as routinely done in FIG. 1A. While the inactive monomer Stat3 protein did not bind DNA response element (FIG. 1C (ii), lane 7), assuming that it interacted with IS3 295, it would be expected to titrate out and diminish IS3 295 levels. This would have translated into restoration of DNA-binding levels of activated Stat3. As originally observed in FIG. 1A (i), pre-incubation with IS3 295 of nuclear extracts containing activated Stat3 significantly decreased the levels of DNA-binding activity in the absence of Stat monomer (FIG. 1C (ii), lanes 1-6). However, when inactive Stat3 monomer protein was added to the nuclear extract, EMSA analysis showed that similar treatment with IS3 295 had diminished effect on the level of Stat3 DNA-binding activity (FIG. 1C (ii), compare lanes 8-14 to lanes 1-6). For example, the presence of inactive Stat3 monomer protein completely restored the DNA-binding activity of active Stat3 in conditions of 1-10 µM IS3 295, where Stat3 activity was hitherto strongly inhibited (FIG. 1C (ii), lanes 11-12 vs. 3-4); recovery of Stat3 DNA-binding activity was only partial with the Stat3 monomer at 30 µM IS3 295 (FIG. 1C (ii), lanes 13 vs 5), perhaps due to higher relative concentration of IS3 295 compared to the amount of Stat3 monomer added. These findings were therefore consistent with the expected results and supported the view that the monomer Stat3 interacted with and titrated out IS3 295, thereby reducing the levels that were available to inhibit active Stat3.

Similar observations were made when inactive Stat1 monomer was present in the nuclear extract and investigated for effect on IS3 295-induced inhibition of Stat3 DNA-binding activity (FIG. 1C (iii), compare lanes 8-12 to lanes 1-6). This suggested that IS3 295 interacted with Stat1 protein. In contrast, the addition of inactive Stat5 monomer or a non-Stat-related, E2F1 protein failed to significantly influence the effect of IS3 295 on Stat3 DNA-binding activity (FIG. 1C (iv), compare lanes 8-14 to lanes 1-6 and FIG. 1C (v), compare lanes 7-12 to lanes 1-6). These results together supported an interaction of IS3 295 with Stat3 protein within the DNA-binding domain, which was independent of the activation status of the protein, and in turn abrogated the binding to its DNA response element.

To investigate the possibility that IS3 295 altered the integrity of the hSIE oligonucleotide probe used in the DNA-binding studies and thereby inhibited Stat3 DNA-binding activity, the oligonucleotide was similarly treated with IS3 295 for 30 minutes, radiolabeled and tested probe for in vitro Stat3 DNA-binding activity. EMSA analysis of nuclear extracts containing activated Stat3 and incubated with the IS3 295-treated radiolabeled hSIE shows that the pretreated hSIE oligonucleotide bound activated protein (compared to non-treated oligonucleotide probe (FIG. 1D, lanes 1 vs. 2), suggesting that the IS3 295 treatment had no observable effect on the in vitro binding activity of Stat3 to the probe. Thus, in the conditions of the in vitro DNA-binding activity assay of Stat3, the presence of IS3 295 did not denature the integrity of the oligonucleotide probe.

To further explore the interaction of IS3 295 with Stat3 protein, assays of in vitro DNA-binding activity were performed with different levels of activated Stat3 protein (1-3 µg total protein) and radiolabeled hSIE oligonucleotide probe, while also varying the concentration of IS3 295. EMSA analysis shows that in vitro Stat3 DNA-binding activity increased with increasing protein amounts (FIG. 2A, lanes 1, 6 and 11). As previously shown in FIG. 1A (i), the presence of IS3 295 caused dose-dependent decrease in the level of Stat3 DNA-binding activity at low (1 µg total protein) Stat3 protein (FIG. 2A, lanes 2-5). However, at higher Stat3 protein (2-3 µg total protein) levels, the decreasing effect of IS3 295 was nearly or completely eliminated (FIG. 2A lanes 6-15), which suggested that increasing levels of Stat3 protein restored the Stat3 DNA-binding activity at concentrations of IS3 295 that otherwise significantly abrogated Stat3 activity when the protein levels were low (FIG. 2A, compare lanes 8-10, 13-15 to lanes 3-5). The restoration in binding at higher Stat3 protein levels suggested available residual active Stat3 protein for binding to radiolabeled DNA response element in the presence of IS3 295, which further supported a possible interaction of IS3 295 with Stat3. Altogether, the findings (FIGS. 1 and 2A) indicate IS3 295 interacts with Stat3 at a putative location within the Stat3 DNA-binding domain.

Example 5

Kinetics of IS3 295-Mediated Inhibition of Stat3 DNA-Binding Activity

Thus far, the evidence suggested a possible interaction of IS3 295 with Stat3 protein within the DNA-binding domain. To further characterize the IS3-Stat3 interaction and its effect on binding to DNA response element, the effects of increasing concentrations of the hSIE oligonucleotide probe were examined. Nuclear extracts of equal total protein were incubated simultaneously with increasing amounts of radiolabeled hSIE probe and IS3 295 for 30 minutes and then subjected to EMSA analysis. Results showed that increasing the amount of radiolabeled hSIE probe increased the level of in vitro DNA-binding activity of Stat3 for the same amount of total protein (FIG. 2A, lanes 1-4, 5-8, 9-12; FIG. 2C, lanes 1, 6, 11 and 16). The level of DNA-binding activity of Stat3 reached a maximum (saturation) at the highest amounts of hSIE (FIG. 2B, lanes 1-4, FIG. 2C, lanes 1, 6, 11 and 16), as evidenced by the plateau levels in the plot of Stat3-DNA bound complex versus amount of hSIE shows (FIG. 2D).

While EMSA analysis showed that at 0.5 µM IS3 295 and higher, DNA-binding activity of Stat3 increasesd with increasing amounts of probe and reached a saturation, this trend was, however, strongly diminished in the presence of high concentrations of IS3 295 compared to control (absent IS3 295) (FIG. 2B, compare each of lanes 9-12, 13-16, and 17-20 to 1-4; FIG. 2C, compare lanes 4, 9, 14, 19 or 5, 10, 15, 20 to 1, 6, 11, 16 or 2, 7, 12, 17 or 3, 8, 13, 18). These observations suggested that increasing the amount of probe failed to overcome the diminishing effect of higher concentrations of IS3 295 and to restore the Stat3 DNA-binding activity to maximal levels observed in control (FIG. 2D). Rather, the findings (FIG. 2D) showed saturations were reached at higher amounts of hSIE probe, albeit representing lower maximal bindings of Stat3 to DNA oligonucleotide probe (lower saturations) for the same amounts of protein at higher concentrations of IS3 295 concentrations (from 0.3-2 µM). Thus, these observations indicated that Stat3 DNA-binding activity cannot be restored with increasing amount of oligonucleotide probe at IS3 concentrations of 1 µM and higher, even though saturation of DNA-binding activity was observed (FIG. 2D). A Lineweaver-Burke (double reciprocal) plot of Stat3-DNA complex versus concentration of hSIE suggested the inhibitory effect on Stat3 DNA-binding activity by IS3 295 could be of the non-competitive type kinetics (FIG. 2E), with changes in affinity and maximum binding.

While the interaction of IS3 295 with Stat3 protein and preclusion of Stat3 DNA-binding activity may suggest that the platinum compound and DNA compete for binding to the same domain of Stat3, our findings do not support a competitive inhibition but rather a non-competitive type. On the basis of known reactions of platinum complexes with thiol-containing biological molecules (34, 53, 55, 56), the expected reaction of IS3 295 with thiol groups of Stat3 would be irreversible, providing no chance of recovery of DNA-binding activity for the IS3 295-treated Stat3 protein by increasing the oligonucleotide amounts, something our study show. In contrast, analyses suggest apparent changes in the binding affinity of Stat3 for the consensus oligonucleotide sequence owing to interaction with IS3 295, an event consistent with modification of the protein. On the other hand, the observation that maximum attainable level of oligonucleotide binding by active Stat3 is diminished with IS3 295 treatment supports a non-competitive type kinetic. Together, these studies raise the potential for IS3 295 to modulate the DNA-binding properties of active Stat3 at different levels, thereby subverting the transcriptional and biological functions of the protein. The ability of IS3 295 to interfere with Stat3 is independent of the activation status of the protein.

Example 6

IS3 295 Selectively Blocked Intracellular Stat3 Signaling and Stat3-Mediated Transformation To investigate the biological importance of IS3 295 inhibition of Stat3 activity, the effects on Stat3 signaling in whole cells were evaluated. In stable cell lines (NIH3T3/v-Src/pLucTKS3 and NIH3T3/v-Src/RLSRE) harboring constitutively active Stat3 and overexpressing Stat3-dependent firefly and Stat3-independent renilla luciferase reporters (38), treatment with IS3 295 strongly suppressed the induction of Stat3-dependent luciferase activity and not the Stat3 independent luciferase activity (FIG. 3). Similarly, treatment with IS3 295 of v-Src-transformed fibroblasts expressing β-galactosidase (β-gal) vector had no effect on the expression of β-gal protein (FIG. 3). These findings indicated that IS3 295 selectively inhibited Stat3 transcriptional activity, consistent with the effect on in vitro Stat3 DNA-binding activity (FIGS. 1 and 2).

To further explore the biological impact of the inhibition of Stat3, IS3 295 was evaluated for effects on Stat3-mediated v-Src transformation (11, 12, 41). In soft-agar growth of v-Src-transformed (NIH3T3/v-Src) fibroblasts, results showed that the treatment of cells with IS3 295 strongly suppressed growth (FIG. 4, left panel). In contrast, similar treatment of v-Ras-transformed NIH3T3/v-Ras growing in soft agar only partially inhibited growth (FIG. 4, right panel).

These findings were consistent with the inhibition of constitutively active Stat3 by IS3 295 and attenuation of growth of v-Src transformed cells, and showed that IS3 295 effect was selective to cells harboring constitutively active Stat3.

Example 7

IS3 295 Induced Block of Cell Cycle and Proliferation—Correlation with Inhibition of Constitutively Active Stat3

The purpose of this example was to further examine the biological effects of IS3 295 and to determine whether any changes might correlate with the inhibition of constitutively active Stat3. Normal NIH3T3 and v-Src-transformed counterparts, human breast cancer cell lines harboring constitutively active Stat3 (MDA-MB-435, MDA-MB-231, and MDA-MB-468) and counterparts that do not harbor Stat3 activity (MDA-MB-453 and MCF-7), as well as human non-small cell lung cancer cell line (A549), human prostate cancer cell line (DU145) and murine multiple myeloma cell line (5TGM1), all of which harbor constitutively active Stat3 (19, 39, 48) were treated with or without IS3 295 for 24 hours. Cells were then harvested for nuclear extract preparation and in vitro Stat3 DNA-binding activity assay with EMSA analysis, or processed for cell proliferation and cell cycle analysis by flow cytometry.

EMSA analysis of Stat3 DNA-binding activity in nuclear extracts prepared from malignant cells harboring constitutively active Stat3 and treated with IS3 295 revealed significant inhibition of constitutive activation of Stat3 in those cells (FIG. 5A). These observations supported the inhibition of Stat3 transcriptional activity (FIG. 3) and together indicated that IS3 295 selectively blocks constitutive activation of Stat3 signaling in diverse cell types. In some cases, "selectively blocks" means that IS3 295 has a greater effect on Stat3 than on other Stat proteins, e.g., Stat1. Normal NIH3T3 and human breast cancer cell line, MDA-MB-453 did not harbor constitutively active Stat3 (FIG. 5A).

Changes in cell proliferation induced by treatment with IS3 295 were assayed in terms of Ki67 proliferation index by immunohistochemistry. The presence of Ki-67 nuclear staining was calculated as the percent positive tumor cells in relation to the total number cells. In contrast to the lack of effect of IS3 295 on the proliferation of normal fibroblasts (NIH3T3) or the human breast cancer cell line MDA-MB-453 that did not harbor persistent Stat3 activity, treatment with 1S3 295 caused significant decreases in Ki67 for the malignant cells harboring constitutively active Stat3 investigated here (FIG. 5B), which correlates with inhibition of Stat3 activity (FIG. 5A).

Figure 6:
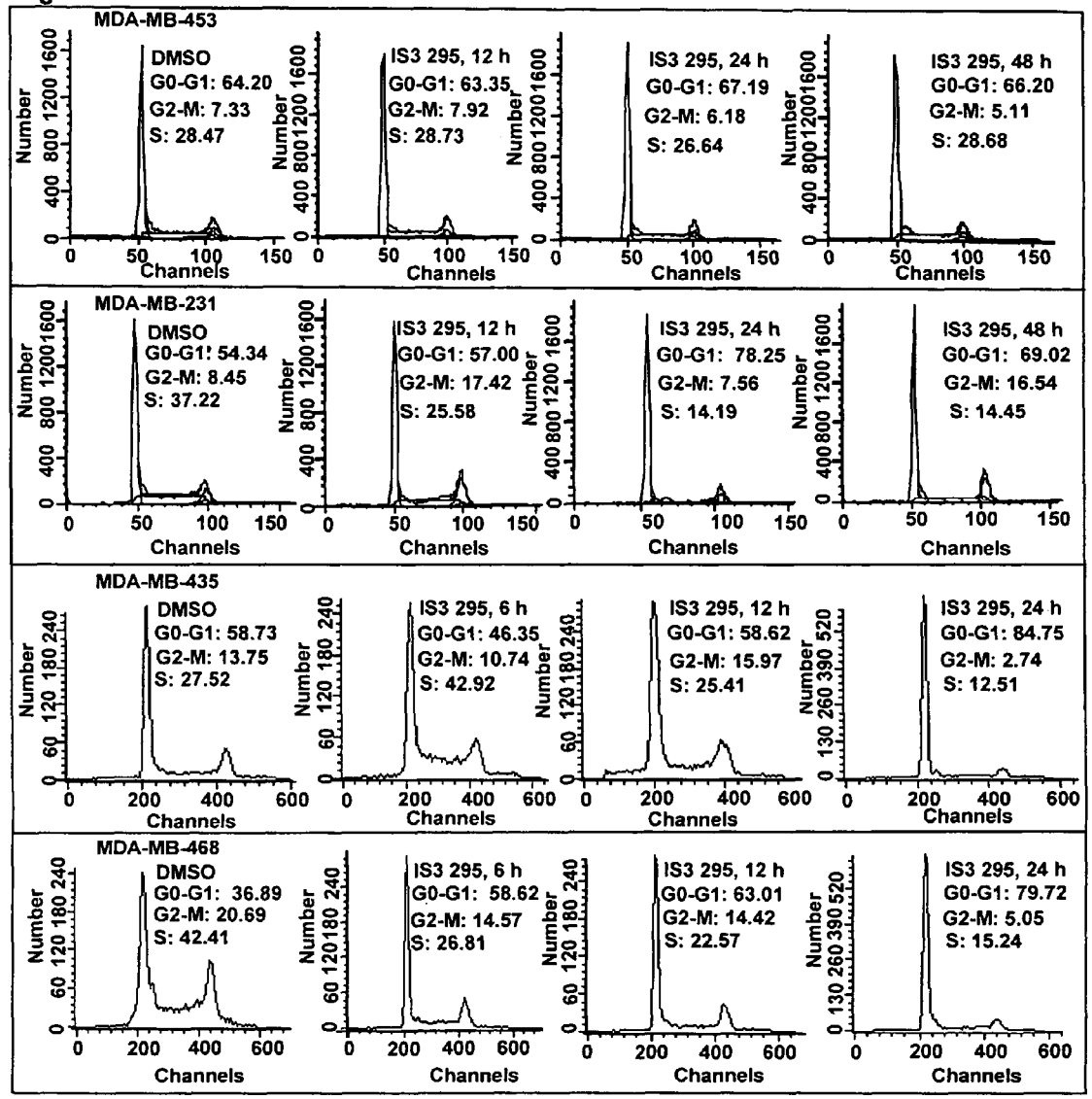
FIG. 6—FIG. 6 shows the results of experiments that analyze relative cellular DNA content using BrdU labeling and flow cytometry. Relative DNA content analysis by BrdU and flow cytometry of human breast cancer cell lines following treatment with or without IS3 295. For each treatment condition, the population of cells determined from the relative DNA content are shown in each panel. Results are the representative of four independent determinations.

In flow cytometric analyses for cell cycle changes in IS3 295-treated and untreated (control) cells exposed to BrdU, results showed that the breast cancer cell line, MDA-MB-231 was arrested at $G_0$-$G_1$ phase following IS3 295 treatment (FIG. 6). Significant decrease in S-phase is also observed, which parallels drop in DNA synthesis, as judged from the level of incorporation of BrdU, and which persists up to 48 hours. Similar results are observed after 6 hours, IS3 295-treatment of breast cancer cell line, MDA-MB-468 (FIG. 6, and data not shown). In the case of MDA-MB-435, same observations are made following 24-hours treatment (FIG. 6). In contrast, no significant change in cell cycle profile was observed when the breast cancer cell line MDA-MB-453 that did not harbor constitutively active was treated with IS3 295 (FIG. 6). These findings together showed that malignant cells harboring persistent elevated Stat3 activity were more sensitive to IS3 295 than cells that did not have persistently elevated Stat3 activity. Further, this was due to the ability of IS3 295 to inhibit constitutively active Stat3.

Example 8

IS3 295-Mediated Apoptosis of Malignant Cells is Dependent on Constitutively Active Stat3

To extend the studies of biological effects of IS3 295 to cell survival, malignant cells harboring persistent Stat3 signaling and those that do not were examined for evidence of apoptosis following treatment with IS3 295. Cells were analyzed for DNA-strand breaks by TUNEL staining. Significant TUNEL staining was detected in v-Src-transformed fibroblast (NIH3T3/v-Src), human breast carcinoma cell lines (MDA-MB-435, MDA-MB-468, MDA-MD-231), human non-small cell lung cancer cell line (A549), human prostate carcinoma cell line (DU145), multiple myeloma cell lines 5TGM1 (mouse) and U266 (human), mouse melanoma cell line (B16), and pancreatic cancer cell line (Panc1), all of which harbored constitutively active Stat3, following treatment with IS3 295 (FIG. 7). In contrast, no TUNEL staining was observed in control (DMSO-treated) cells, mouse fibroblast (NIH3T3), and human breast cancer cell line (MDA-MB-453) that did not contain aberrant Stat3 activity and were treated with IS3 295 (FIG. 7). The incidence of apoptosis correlated with the prevalence of constitutively active Stat3 in malignant cells (FIG. 7, lower panel). These results together indicated differences in sensitivity of cells to IS3 295, which are dependent on the activation status of Stat3 inside cells. The susceptible malignant cells were those that harbor constitutively active Stat3, which undergo cell cycle arrest and apoptosis in response to IS3 295, consistent with previous reports of induction of apoptosis of transformed and tumor cells following inhibition of persistent Stat3 activity (15, 18-20, 35, 39, 49).

To investigate potential molecular changes downstream from Stat3 that contributed to the biological responses induced by IS3 295, in situ detection and Western Blot analyses were conducted for cell cycle and apoptosis regulators. Results showed that Cyclin D1 was significantly diminished in v-Src-transformed mouse fibroblast (NIH3T3/v-Src) and human breast cancer cell line (MDA-MB-435) in response to IS3 295-induced inhibition of Stat3 activation (FIG. 8). Similar observation was made for the anti-apoptotic Bcl-xL protein in both malignant cell lines, which harbored constitutively active Stat3, following treatment with IS3 295 (FIG. 8). These findings paralleled the cell cycle or proliferation changes and the induction of apoptosis by the IS3 295 treatment (FIGS. 5, 6 and 7), and suggested that inhibition of constitutively active Stat3 by IS3 295 blocks Cyclin D1 and Bcl-xL induction, and contributed to cell cycle arrests and apoptosis of malignant cells harboring aberrant Stat3 signaling.

Example 9

Use of IS3 295 to Reduce Tumors or Melanoma in a Mouse Model

The anti-tumor efficacy of IS3 295 is evaluated by using a mouse model of colon tumors harboring constitutively active Stat3. Six-week old female C57BL and Balb/C mice are purchased from the National Cancer Institute (Frederick, Md.) and maintained in the institutional animal facilities approved by the American Association for Accreditation of Laboratory Animal Care. C57BL and Balb/C mice are shaved in the left flank area and injected subcutaneously with $2\times10^5$ melanoma B16 or colon carcinoma CT26 cells in 100 μl of PBS respectively. After 5 to 10 days, tumors with a diameter of 3 to 6 mm are established. The animals are stratified so that the mean tumor sizes in all treatment groups were nearly identical. Tumor size is calculated according to the formula $V=0.52\times a^2\times b$, where a is the smallest superficial diameter and b is the largest superficial diameter.

Mouse colon tumor-bearing mice are given i.v. injections with IS3 295 on days 1, 4, 7, 10, and 12 following implantation of the tumor. The tumor size is measured every 3 days to determine the anti-tumor effect of IS3 295. Likewise, for melanoma, the size of the melanoma is monitored on a regular basis to determine the anti-proliferative effects of IS3 295 on the melanoma.

REFERENCES

The following references are hereby incorporated in their entirety.

1. Darnell, J. E., Jr., Kerr, I. M., and Stark, G. R. (1994) Science 264, 1415-1421.
2. Schindler, C., and Darnell, J. E., Jr. (1995) Annu. Rev. Biochem. 64, 621-651.
3. Darnell, J. E., Jr. (1997) Science 277, 1630-1635.
4. Stark, G. R., Kerr, I. M., Williams, B. R., Silverman, R. H., and Schreiber, R. D. (1998) Annu. Rev. Biochem. 67, 227-264.
5. Bromberg, J. F., Horvath, C. M., Wen, Z., Schreiber, R. D., and Darnell, J. E., Jr. (1996) Proc. Natl. Acad. Sci. USA 93, 7673-7678.
6. Fukada, T., Hibi, M., Yamanaka, Y., Takahashi-Tezuka, M., Fujitani, Y., Yamaguchi, T., Nakajima, K., and Hirano, T. (1996) Immunity 5, 449-460.
7. Kotenko, S. V., and Pestka, S. (2000) Oncogene 19, 2557-2565.
8. Smithgall, T. E., Briggs, S. D., Schreiner, S., Lerner, E. C., Cheng, H., and Wilson, M. B. (2000) Oncogene 19, 2612-2618.
9. Hirano, T., Ishihara, K., and Hibi, M. (2000) Oncogene 19, 2548-2556.
10. Akira, S. (2000) Oncogene 19, 2607-2611.
11. Turkson, J., Bowman, T., Garcia, R., Caldenhoven, E., De Groot, R. P., and Jove, R. (1998) Mol. Cell. Biol. 18, 2545-2552.
12. Bromberg, J. F., Horvath, C. M., Besser, D., Lathem, W. W., and Darnell, J. E., Jr. (1998) Mol. Cell. Biol. 18, 2553-2558.
13. Garcia, R., Yu, C. L., Hudnall, A., Catlett, R., Nelson, K. L., Smithgall, T., Fujita, D. J., Ethier, S. P., and Jove, R. (1997) Cell Growth Diff. 8, 1267-1276.
14. Nielsen, M., Kaltoft, K., Nordahl, M., Ropke, C., Geisler, C., Mustelin, T., Dobson, P., Svejgaard, A., and Odum, N. (1997) Proc. Natl. Acad. Sci. USA 94, 6764-6769.
15. Catlett-Falcone, R., Landowski, T. H., Oshiro, M. M., Turkson, J., Levitzki, A., Savino, R., Ciliberto, G., Moscinski, L., Femandez-Luna, J. L., Nunez, G., Dalton, W. S., and Jove, R. (1999) Immunity 10, 105-115.
16. Nielsen, M., Kaestel, C. G., Eriksen, K. W., Woetmann, A., Stokkedal, T., Kaltoft, K., Geisler, C., Ropke, C., and Odum, N. (1999) Leukemia 13, 735-738.
17. Bromberg, J. (2000) Breast Cancer Res. 2, 86-90.
18. Grandis, J. R., Drenning, S. D., Zeng, Q., Watkins, S. C., Melhem, M. F., Endo, S., Johnson, D. E., Huang, L., He, Y., and Kim, J. D. (2000) Proc. Natl. Acad. Sci. U.S.A. 97, 4227-4232.
19. Garcia, R., Bowman, T. L., Niu, G., Yu, H., Minton, S., Muro-Cacho, C. A., Cox, C. E., Falcone, R., Fairclough, R., Parson, S., Laudano, A., Gazit, A., Levitzki, A., Kraker, A., and (2001) Oncogene 20, 2499-2513.
20. Epling-Burnette, P. K., Lui, J. H., Catlette-Falcone, R., Turkson, J., Oshiro, M., Kothapalli, R., Li, Y., Wang, J.-M., Yang-Yen, H.-F., Karras, J., Jove, R., and Loughran, T. P., Jr. (2001) J. Clin. Invest. 107, 351-362.
21. Bowman, T., Garcia, R., Turkson, J., and Jove, R. (2000) Oncogene 19, 24742488.
22. Turkson, J., and Jove, R. (2000) Oncogene 19, 6613-6626.
23. Song, J. I., and Grandis, J. R. (2000) Oncogene 19, 2489-2495.
24. Coffer, P. J., Koenderman, L., and de Groot, R. P. (2000) Oncogene 19, 2511.
25. Lin, T. S., Mahajan, S., and Frank, D. A. (2000) Oncogene 19, 2496-2504.
26. Buettner, R., Mora, L. B., and Jove, R. (2002) Clin. Cancer Res. 8, 945-954.
27. Yu, H., and Jove, R. (2004) Nat. Rev. Cancer 4, 97-105.
28. Turkson, J. (2004) Expert Opin Ther Targets 8, 409-422.
29. Niu, G., Heller, R., Catlett-Falcone, R., Coppola, D., Jaroszeski, M., Dalton, W., Jove, R., and Yu, H. (1999) Cancer Res. 59, 5059-5063.
30. Oshiro, M. M., Landowski, T. H., Catlett-Falcone, R., Hazlehurst, L. A., Huang, M., Jove, R., and Dalton, W. S. (2001) Clin. Cancer Res. 7, 4262-4271.
31. Sanchez-Perez, I., Murguia, J. R., and Perona, R. (1998) Oncogene 16, 533-540.
32. Persons, D. L., Yazlovitskaya, E. M., Cui, W., and Pelling, J. C. (1999) Clin. Cancer. Res. 5, 1007-1014.
33. Bose, R. N. (2002) Mini. Rev. Med. Chem. 2, 103-111.
34. Siddik, Z. H. (2003) Oncogene 22, 7265-7279.
35. Turkson, J., Zhang, S., Palmer, J., Kay, H., Stanko, J., Mora, L. B., Sebti, S., Yu, H., and Jove, R. (2004) Mol. Cancer Ther. 3, 1-10.
36. Johnson, P. J., Coussens, P. M., Danko, A. V., and Shalloway, D. (1985) Mol. Cell. Biol. 5, 1073-1083.
37. Yu, C. L., Meyer, D. J., Campbell, G. S., Larner, A. C., Carter-Su, C., Schwartz, J., and Jove, R. (1995) Science 269, 81-83.
38. Turkson, J., Ryan, D., Kim, J. S., Zhang, Y., Chen, Z., Haura, E., Laudano, A., Sebti, S., Hamilton, A. D., and Jove, R. (2001) J. Biol. Chem. 276, 45443-45455.
39. Mora, L. B., Buettner, R., Seigne, J., Diaz, J., Ahmad, N., Garcia, R., Bowman, T., Falcone, R., Fairclough, R., Cantor, A., Muro-Cacho, C., Livingston, S., Karras, J., Pow-Sang, J., and Jove, R. (2002) Cancer Res 62, 6659-6666.
40. Oyajobi, B. O., Franchin, G., Williams, P. J., Pulkrabek, D., Gupta, A., Munoz, S., Grubbs, B., Zhao, M., Chen, D., Sherry, B., and Mundy, G. R. (2003) Blood 102, 311-319. Epub 2003 March 2020.
41. Turkson, J., Bowman, T., Adnane, J., Zhang, Y., Djeu, J. Y., Sekharam, M., Frank, D. A., Holzman, L. B., Wu, J., Sebti, S., and Jove, R. (1999) Mol. Cell. Biol. 19, 7519-7528.
42. Zhang, D., Sun, M., Samols, D., and Kushner, I. (1996) J. Biol. Chem. 271, 95039509.
43. Yamauchi, K., Holt, K., and Pessin, J. E. (1993) J. Biol. Chem. 268, 14597-14600.
44. Zhang, Y., Turkson, J., Carter-Su, C., Smithgall, T., Levitzki, A., Kraker, A., Krolewski, J. J., Medveczky, P., and Jove, R. (2000) J. Biol. Chem. 275, 2493524944.
45. Wagner, B. J., Hayes, T. E., Hoban, C. J., and Cochran, B. H. (1990) EMBO J. 9, 4477-4484.

46. Gouilleux, F., Moritz, D., Humar, M., Moriggl, R., Berchtold, S., and Groner, B. (1995) Endocrinology 136, 5700-5708.

47. Seidel, H. M., Milocco, L. H., Lamb, P., Darnell, J. E., Jr., Stein, R. B., and Rosen, J. (1995) Proc. Natl. Acad. Sci. U. S. A. 92, 3041-3045.

48. Song, L., Turkson, J., Karras, J. G., Jove, R., and Haura, E. B. (2003) Oncogene 22, 4150-4165.

49. Bowman, T., Broome, M., Sinibaldi, N., Wharton, W., Pledger, W. J., Sedivy, J., Irby, R., Yeatman, T., Coumeidge, S. A., and Jove, R. (2000) Proc. Natl. Acad. Sci. U. S. A. 98, 7319-7324.

50. Darnell, J. E., Jr. (2002) Nat. Rev. Cancer 2, 740-749.

51. Wang, G., Reed, E., and Li, Q. Q. (2004) Oncol Rep 12, 955-965.

52. Trynda-Lemiesz, L., Kozlowski, H., and Keppler, B. K. (1999) J Inorg Biochem 77, 141-146.

53. Allain, P., Heudi, O., Cailleux, A., Le Bouil, A., Larra, F., Boisdron-Celle, M., and Gamelin, E. (2000) Drug Metab Dispos 28, 1379-1384.

54. Trynda-Lemiesz, L., and Luczkowski, M. (2004) J Inorg Biochem 98, 1851-1856.

55. Heudi, O., Mercier-Jobard, S., Cailleux, A., and Allain, P. (1999) Biopharm Drug 20, 107-116.

56. Heudi, O., Brisset, H., Cailleux, A., and Allain, P. (2001) Int J Clin Pharmacol Ther 349.

57. Becker, S., Groner, B., and Muller, C. W. (1998) Nature 394, 145-151.

58. Perez, J. M., Kelland, L. R., Montero, E. I., Boxall, F. E., Fuertes, M. A., Alonso, C., and Navarro-Ranninger, C. (2003) Mol Pharmacol 63, 933-944.

59. Bromberg, J. F., Wrzeszczynska, M. H., Devgan, G., Zhao, Y., Pestell, R. G., Albanese, C., and Darnell, J. E., Jr. (1999) Cell 98, 295-303.

60. Sinibaldi, N., Wharton, W., Turkson, J., Bowman, T., Pledger, W. J., and Jove, R. (2000) Oncogene 19, 5419-5427.

---

What is claimed is:

1. A method of inducing apoptosis in a malignant cell comprising contacting the malignant cell with IS3 295 having the structure:

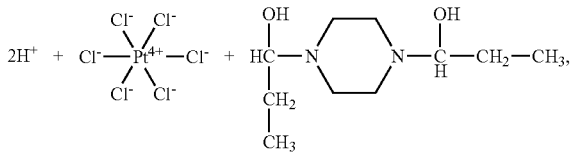

wherein the malignant cell has constitutively activated Stat3 and wherein the malignant cell is selected from the group consisting of breast cancer cell, non-small cell lung cancer cell, myeloma cell, and colon tumor cell.

2. The method of claim 1 wherein the malignant cell is human cells.

3. The method of claim 1 wherein the malignant cell is non-human cells.

4. A method of inducing apoptosis in a malignant cell comprises administering an amount of IS3 295 thereof comprising administering to the individual an amount of IS3 295 having the structure:

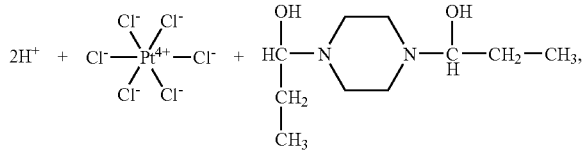

effective for reducing malignant cell growth in the individual, wherein the malignant cell has constitutively activated Stat3 and wherein the malignant cell is selected from the group consisting of breast cancer cell, non-small cell lung cancer cell, myeloma cell, and colon tumor cell.

5. A method for inducing apoptosis comprising contacting a tumor cell with IS3 295 having the structure:

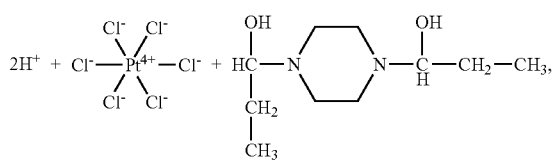

in an amount sufficient to suppress the tumor growth, wherein the tumor cell is known to express Stat3 and wherein the tumor cell is selected from the group consisting of breast cancer cell, non-small cell lung cancer cell, myeloma cell, and colon tumor cell.

6. The method of claim 5 wherein the contact between the tumor cell and IS3 295 is in vitro.

7. The method of claim 5 wherein the contact between the tumor cell and IS3 295 is in vivo.

* * * * *